United States Patent
Morero et al.

(10) Patent No.: US 10,737,071 B2
(45) Date of Patent: Aug. 11, 2020

(54) SPLITTABLE SHEATH

(71) Applicant: Medtronic, Inc., Minneapolis, MN (US)

(72) Inventors: Massimo Morero, Turin (IT); Andrea Sassi, Brescia (IT)

(73) Assignee: MEDTRONIC, INC., Minneapolis, MN (US)

( * ) Notice: Subject to any disclaimer, the term of this patent is extended or adjusted under 35 U.S.C. 154(b) by 169 days.

(21) Appl. No.: 15/875,318

(22) Filed: Jan. 19, 2018

(65) Prior Publication Data

US 2019/0224458 A1    Jul. 25, 2019

(51) Int. Cl.

| A61M 31/00 | (2006.01) |
|---|---|
| A61M 37/00 | (2006.01) |
| A61M 25/10 | (2013.01) |
| A61M 25/06 | (2006.01) |
| A61L 29/04 | (2006.01) |
| A61L 29/06 | (2006.01) |
| A61L 29/16 | (2006.01) |

(52) U.S. Cl.
CPC .......... *A61M 25/10* (2013.01); *A61L 29/041* (2013.01); *A61L 29/06* (2013.01); *A61L 29/16* (2013.01); *A61M 25/0668* (2013.01); *A61M 25/104* (2013.01); *A61M 2025/0675* (2013.01); *A61M 2025/0681* (2013.01); *A61M 2025/105* (2013.01); *A61M 2025/1081* (2013.01); *A61M 2205/0222* (2013.01)

(58) Field of Classification Search
CPC .. A61M 2025/0675; A61M 2025/1081; A61M 2025/0681; A61M 25/068
See application file for complete search history.

(56) References Cited

U.S. PATENT DOCUMENTS

| 4,983,168 | A | 1/1991 | Moorehead |
|---|---|---|---|
| 5,188,605 | A | 2/1993 | Sleep |
| 5,647,857 | A | 7/1997 | Anderson et al. |
| 5,868,719 | A | 2/1999 | Tsukernik |
| 5,964,730 | A | 10/1999 | Williams et al. |
| 6,110,146 | A | 8/2000 | Berthiaume et al. |
| 6,592,548 | B2 | 7/2003 | Jayaraman |
| 7,105,013 | B2 | 9/2006 | Durcan |
| 8,414,528 | B2 | 4/2013 | Liu et al. |
| 8,852,257 | B2 | 10/2014 | Liu et al. |
| 9,072,590 | B2 | 7/2015 | Wang et al. |
| 9,119,741 | B2 | 9/2015 | Liu et al. |
| 2010/0094392 | A1* | 4/2010 | Nguyen ................ A61F 2/2427 623/1.11 |
| 2011/0270226 | A1 | 11/2011 | Kocur et al. |

(Continued)

OTHER PUBLICATIONS

Extended Search Report from counterpart European Application No. 19150998.3, dated Jun. 18, 2019, 10 pp.

(Continued)

*Primary Examiner* — Rebecca E Eisenberg

(74) *Attorney, Agent, or Firm* — Shumaker & Sieffert P.A.

(57) ABSTRACT

In some examples, a splittable sheath includes a sheath body defining a lumen configured to receive an expandable balloon of a catheter, and a tab extending from a proximal end or a distal end of the sheath body. The tab includes a major surface having an outer edge defining a serpentine shape. Outward movement of the tab relative to a central longitudinal axis of the sheath body causes splitting of the sheath body.

28 Claims, 18 Drawing Sheets

(56) References Cited

U.S. PATENT DOCUMENTS

| | | |
|---|---|---|
| 2013/0018309 A1 | 1/2013 | Ewing et al. |
| 2013/0090624 A1 | 4/2013 | Munsinger |
| 2014/0379065 A1 | 12/2014 | Johnson et al. |
| 2015/0088241 A1 | 3/2015 | Liu et al. |
| 2015/0328028 A1 | 11/2015 | Wang et al. |
| 2016/0058983 A1 | 3/2016 | Poker et al. |
| 2018/0043138 A1 | 2/2018 | Chu |
| 2018/0078744 A1* | 3/2018 | Trocke .............. A61M 25/1002 |

OTHER PUBLICATIONS

U.S. Appl. No. 15/875,356, filed Jan. 19, 2018, naming inventors Connors et al.
U.S. Appl. No. 15/875,343, filed Jan. 19, 2018, naming inventors Traxler et al.
U.S. Appl. No. 15/875,372, filed Jan. 19, 2018, naming inventors Kantor et al.
U.S. Appl. No. 15/875,331, filed Jan. 19, 2018, naming inventor Chiara Pedroni.
Response to Extended Search Report from counterpart European Application No. 19150998.3, dated Sep. 9, 2019, 22 pp.

* cited by examiner

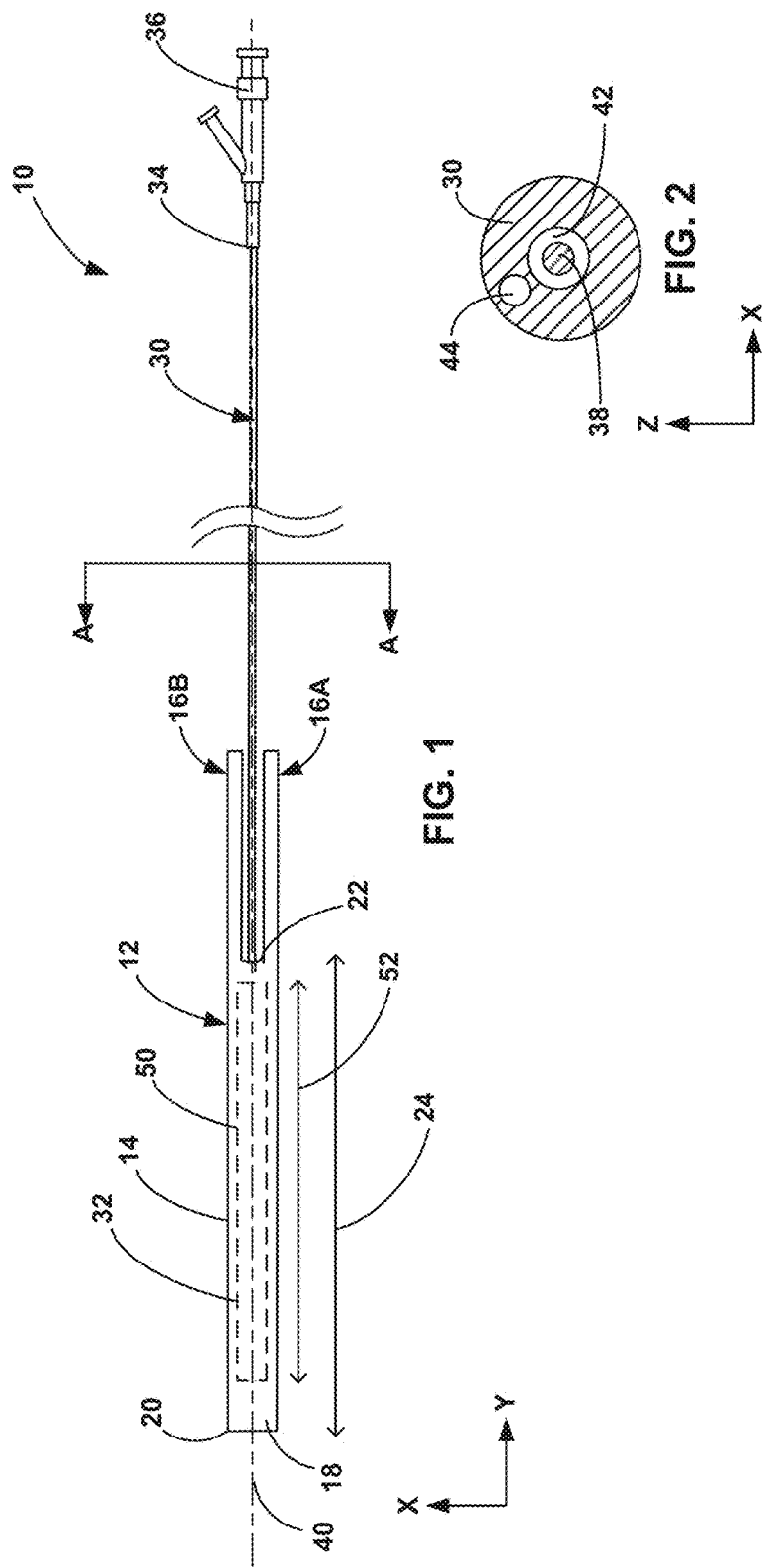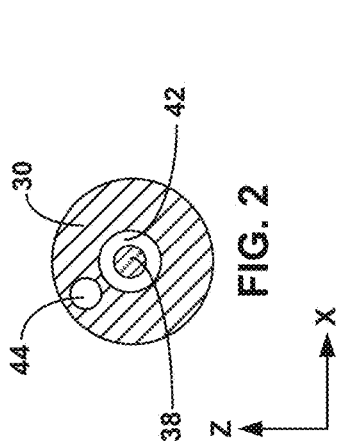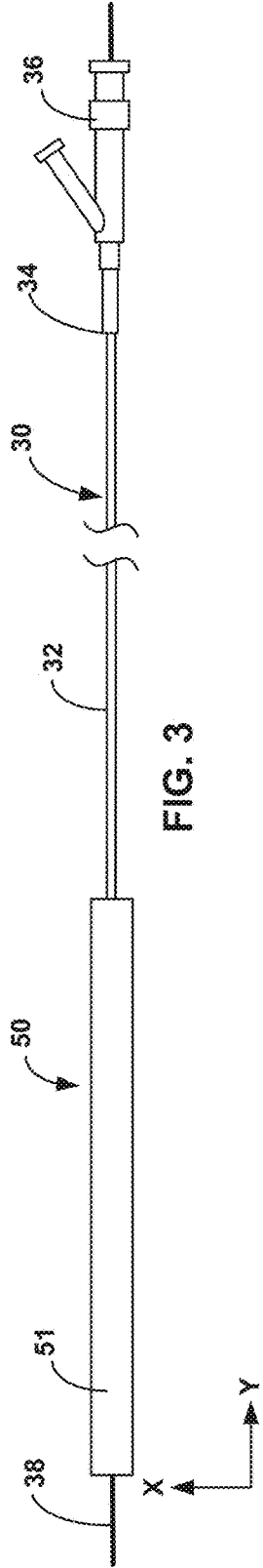

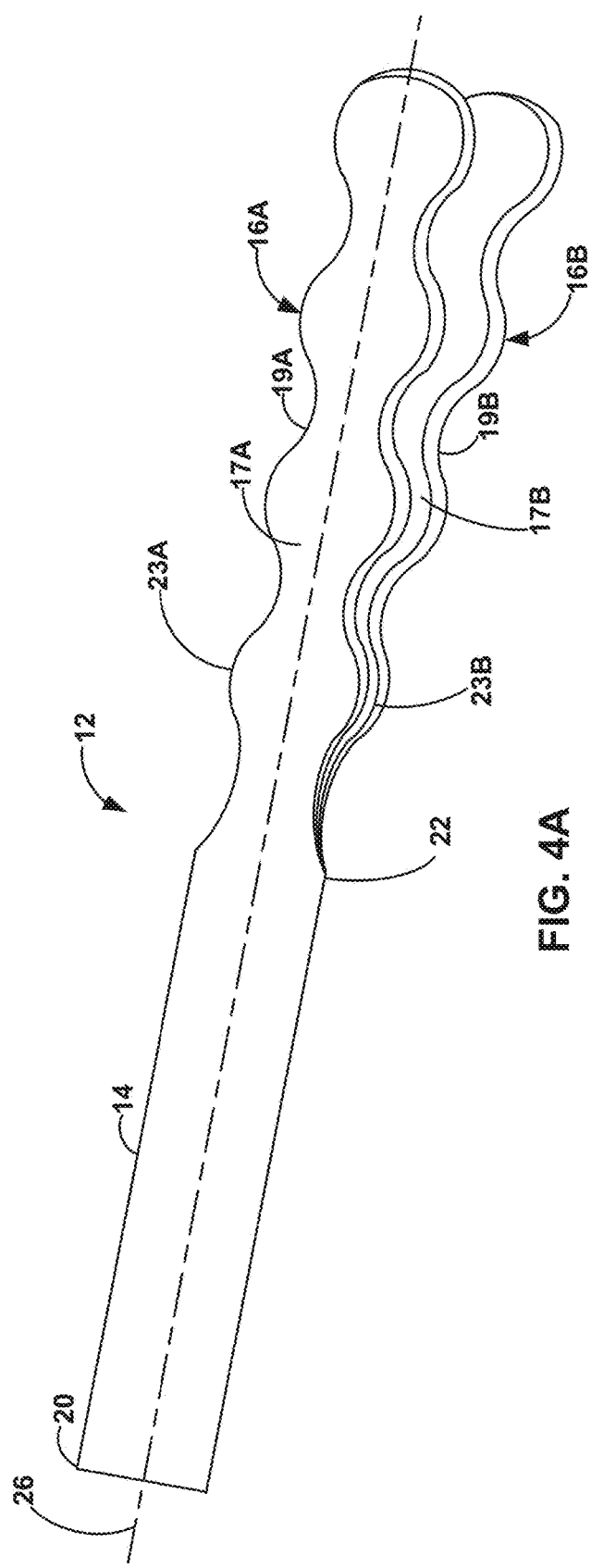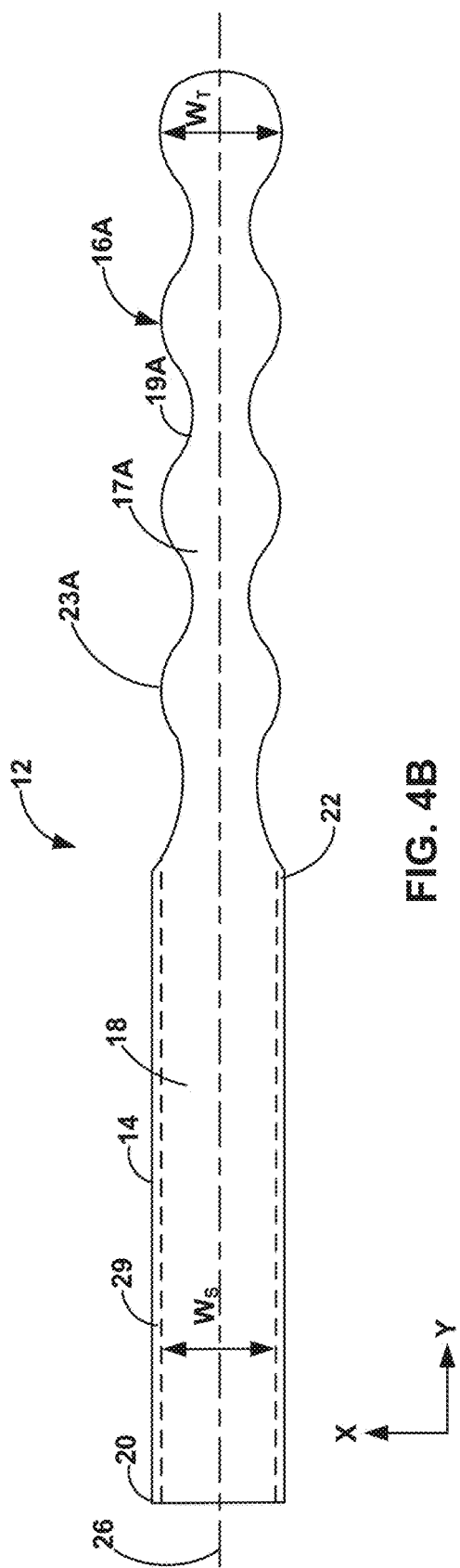
FIG. 4A
FIG. 4B

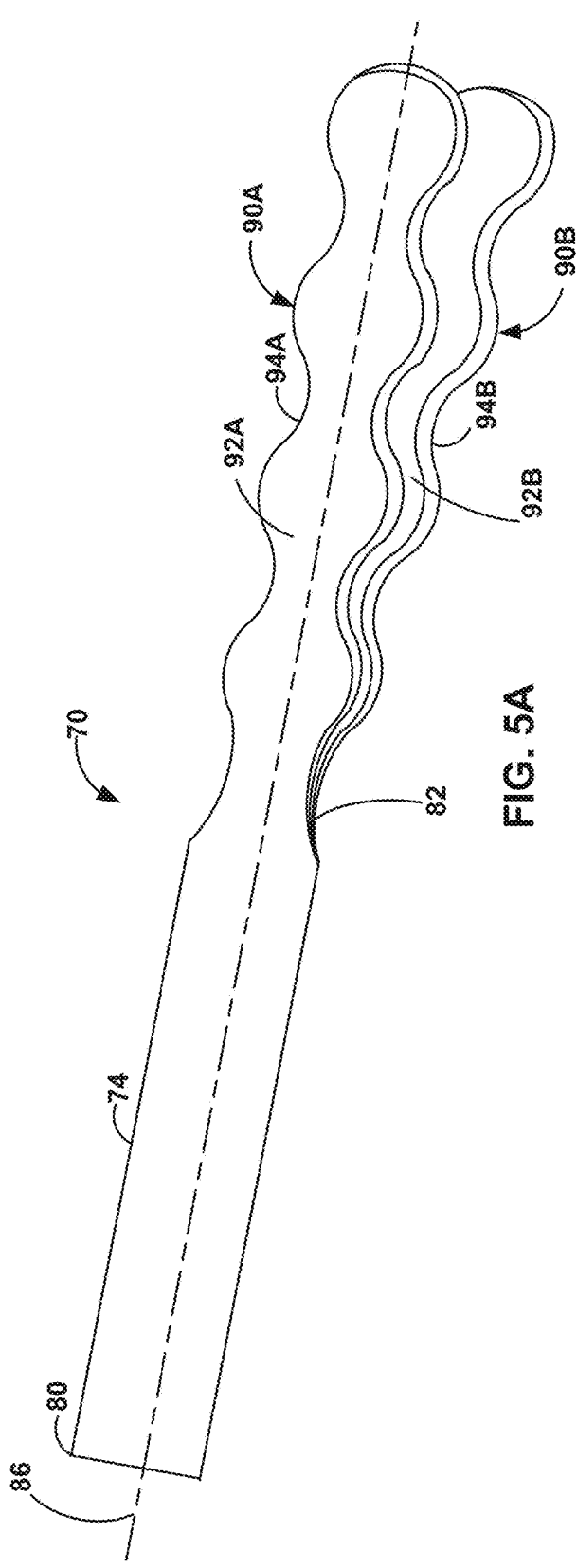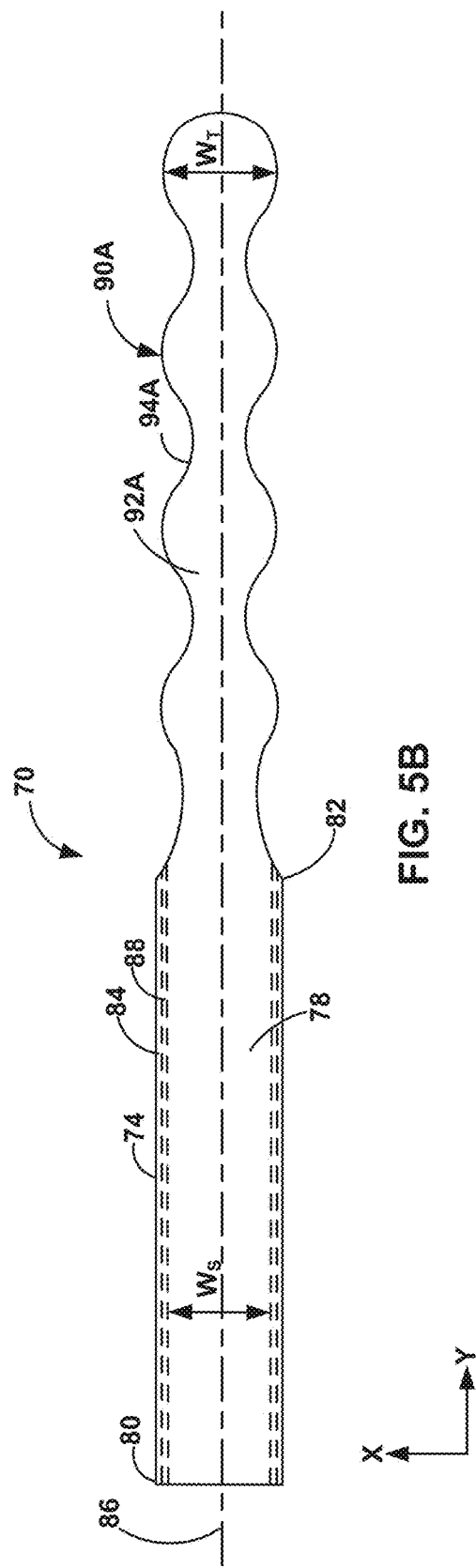
FIG. 5A
FIG. 5B

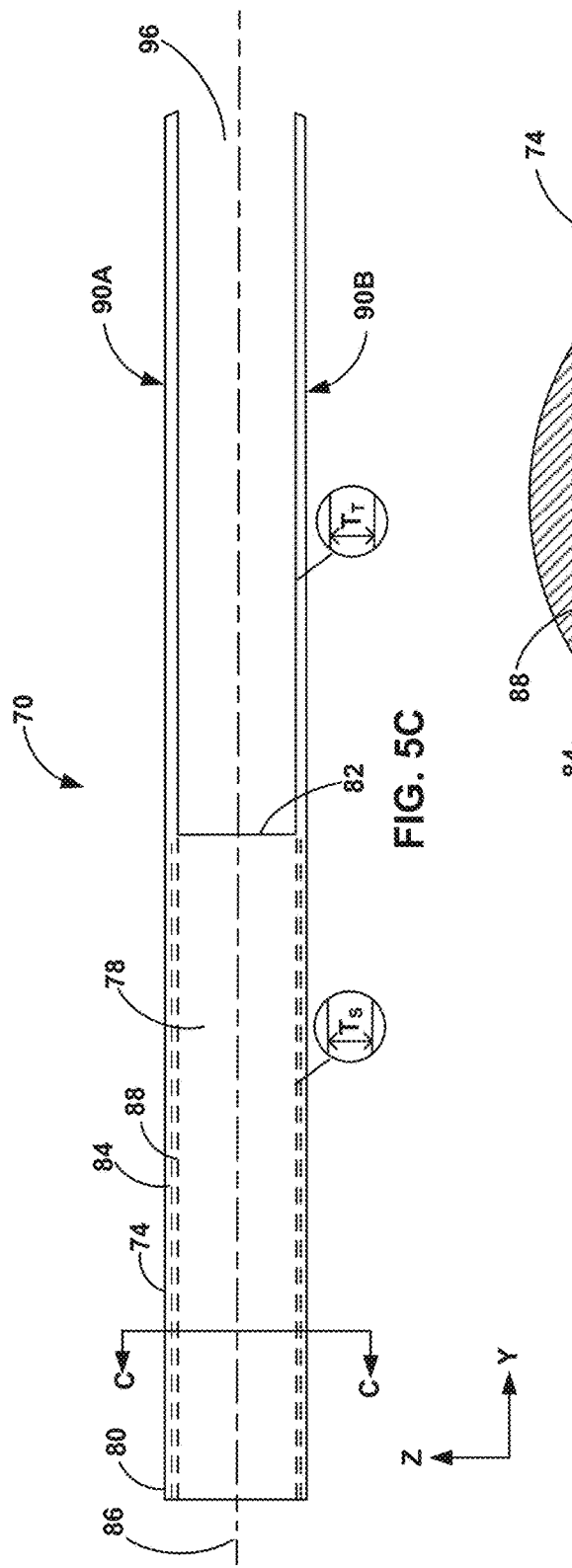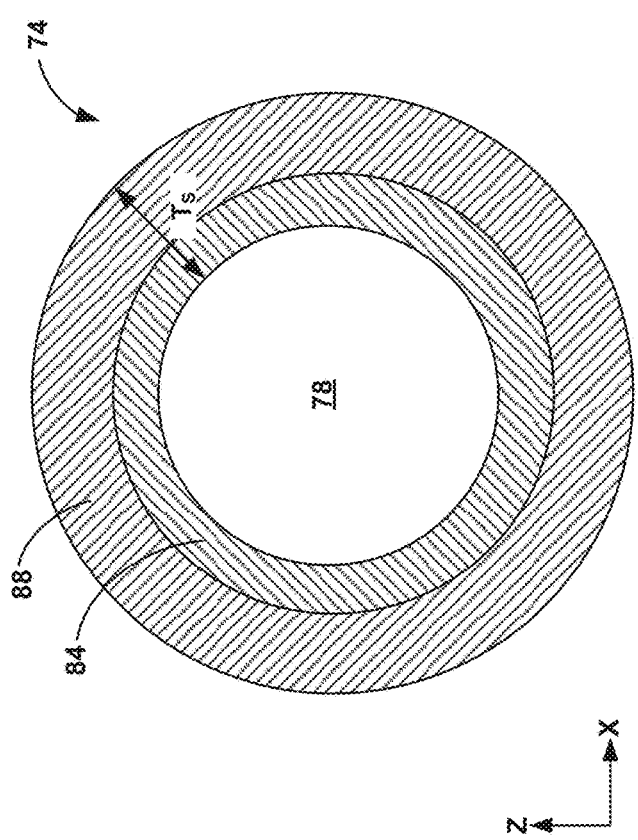

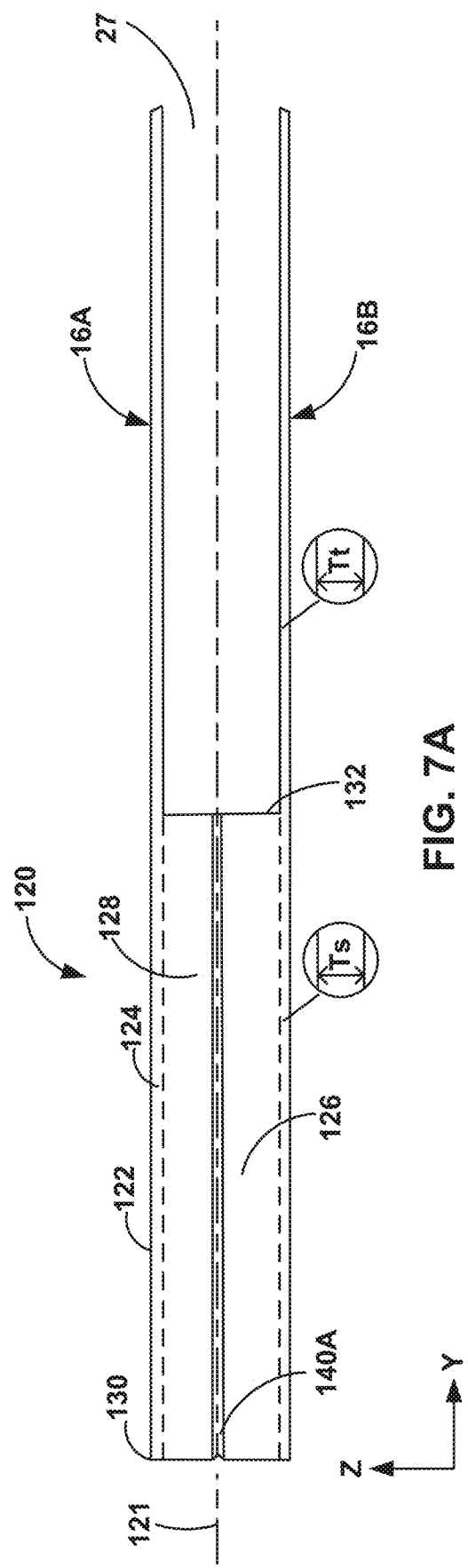

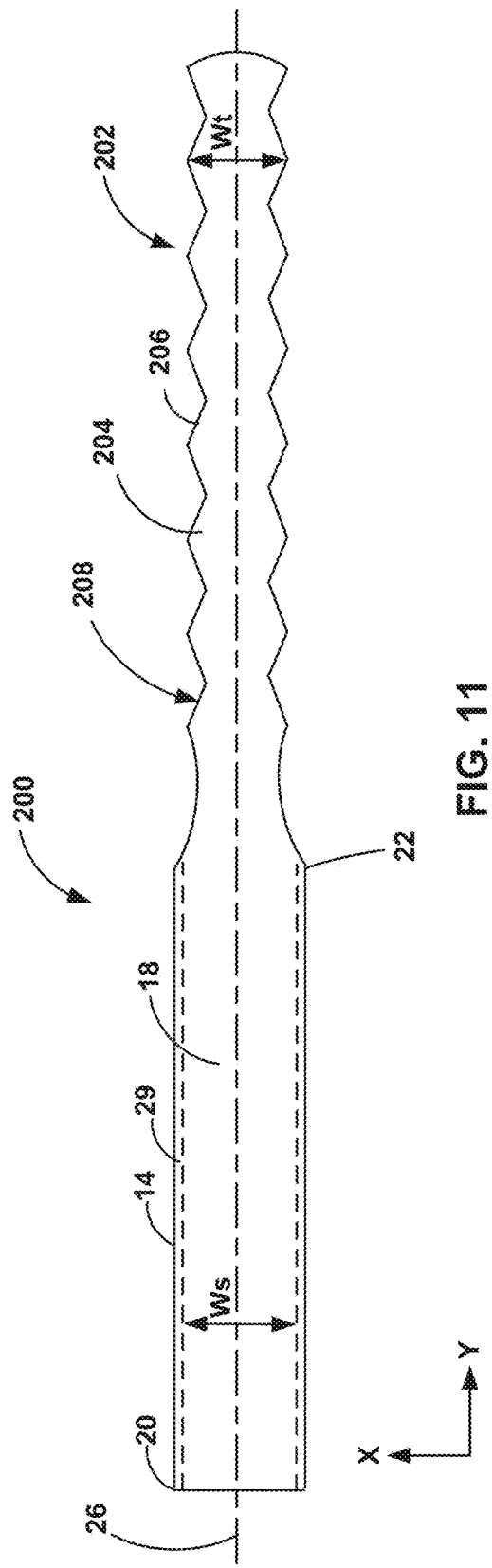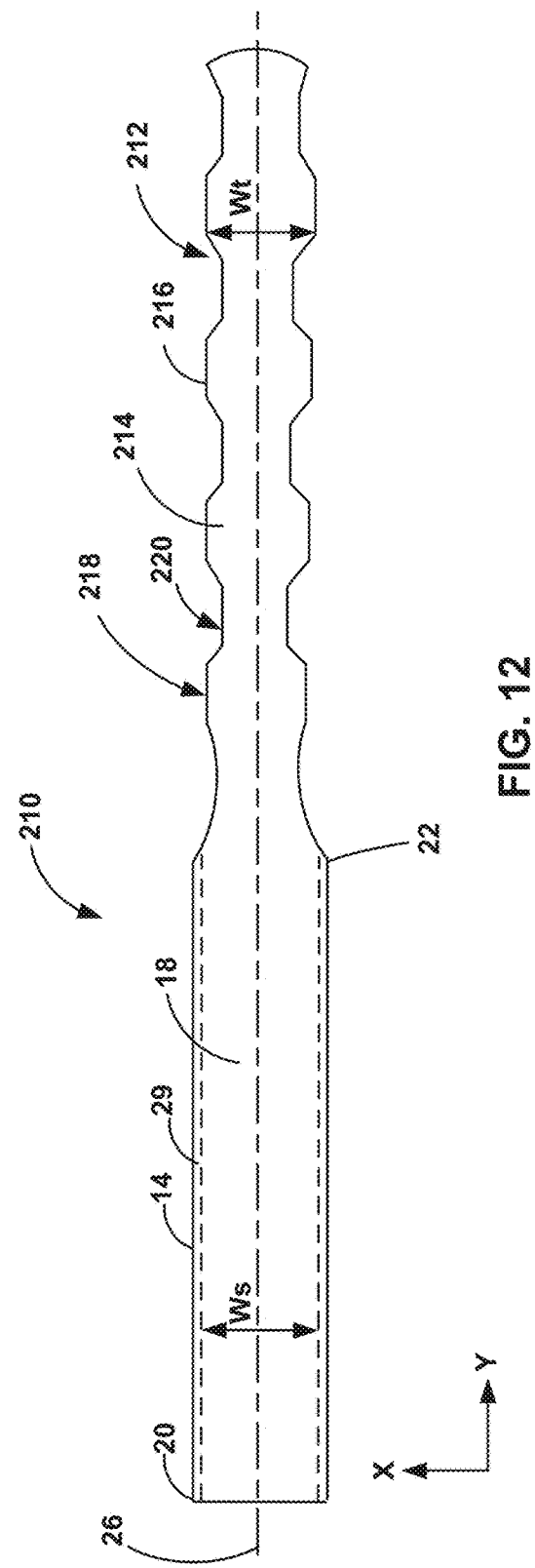

SPLITTABLE SHEATH

TECHNICAL FIELD

The disclosure relates generally to sheaths for medical devices, and more specifically to splittable sheaths, and to methods of manufacturing and using sheaths, and medical devices assemblies including the sheaths.

BACKGROUND

Portions of the vasculature of a patient may be treated to restore adequate blood flow in an occluded blood vessel. Conditions for which blood-flow restoration may be indicated include atherosclerosis and other conditions that may cause narrowing of a lumen of a blood vessel. In some examples, a system for restoring adequate blood flow may include an expandable balloon positioned on a catheter and received within a sheath. During treatment, a clinician may advance the balloon through the sheath and into the vasculature of the patient, navigate the balloon to a treatment site within a target vessel, and then expand the balloon to restore patency of the target vessel. Some balloon sheaths may be configured to be longitudinally split into two portions to enable a clinician to remove the sheath from the catheter once the balloon has been advanced through the sheath. In some examples, expandable balloons may include a drug coating to help prevent re-stenosis of the target vessel.

SUMMARY

This disclosure describes example splittable sheaths that can be used, for example, to protect an expandable balloon prior to the introduction of the balloon into the vasculature of a patient. The disclosure also describes example devices that include a splittable sheath defining a lumen, and an expandable balloon positioned on a catheter and configured to be received within the lumen of the splittable sheath. In some examples, a splittable sheath includes one or more tabs extending from a proximal end or a distal end of a sheath body, the tabs being configured such that outward movement of the tab relative to a central longitudinal axis of the sheath body causes splitting of the sheath body. A clinician may grasp the one or more tabs and move the tabs relative to the central longitudinal axis of the sheath body to split the sheath into multiple portions, which may aid removal of the sheath from the catheter during a medical procedure.

The one or more tabs of the sheath may include a major surface having an outer edge that defines a shape, such as a serpentine shape. The shape of the outer edge of the major surface of the tab may provide a gripping surface for the clinician's fingers or a tool used by the clinician as the clinician grasps the tab to split the sheath. Also described herein are methods of using devices that comprise the balloon catheter and the splittable sheath, as well as methods of making the splittable sheath.

In a first example, a splittable sheath including a sheath body defining a lumen configured to receive an expandable balloon of a catheter, and a tab extending from a proximal end or a distal end of the sheath body, wherein outward movement of the tab relative to a central longitudinal axis of the sheath body causes splitting of the sheath body, and wherein the tab includes a major surface having an outer edge defining a serpentine shape.

In a second example, a device includes the splittable sheath of the first example, and a catheter including a catheter body and an expandable balloon positioned on the catheter body.

In a third example relating to the device of the first and second examples, a width of the tab is substantially the same as a width of the lumen of the sheath body, the width being measured in a direction perpendicular to the central longitudinal axis of the sheath body.

In a fourth example relating to the device of any of the first through third examples, the tab is integrally formed with the sheath body.

In a fifth example relating to the device of any of the first through fourth examples, the tab comprises a first tab including a first major surface having a first outer edge defining a first serpentine shape, the sheath further comprising a second tab extending from the proximal end or the distal end of the sheath body, wherein outward movement of the second tab relative to the first tab causes splitting of the sheath body, the second tab including a second major surface having a second outer edge defining a second serpentine shape.

In a sixth example relating to the device of any of the first through fifth examples, an outer wall of the sheath body defines at least one groove extending longitudinally along an outer surface of the sheath body, and wherein the sheath body is configured to split along the at least one groove when the first tab and the second tab are moved outward relative to the central longitudinal axis of the sheath body.

In a seventh example relating to the device of the sixth example, the at least one groove comprises a first groove and a second groove, wherein outward movement of the tab relative to the central longitudinal axis of the sheath body causes splitting of the sheath body along the first and second grooves.

In an eighth example relating to the device of the sixth example, the at least one groove comprises a first groove and a second groove positioned on opposite sides of the central longitudinal axis of the sheath body.

In a ninth example relating to the device of any of the sixth through eighth examples, the at least one groove is aligned with the outer edge of the tab along an axis parallel to the central longitudinal axis of the sheath body.

In a tenth example relating to the device of any of the sixth through ninth examples, each groove of the at least one groove extends from the outer surface of the outer wall of the sheath body through about 50% to about 90% of a thickness of the outer wall of the sheath body.

In an eleventh example relating to the device of any of the sixth through tenth examples, each groove of the at least one groove extends along about 2% to about 20% of a perimeter of a cross-section of the sheath body taken orthogonal to the central longitudinal axis of the sheath body.

In a twelfth example relating to the device of any of the first through eleventh examples, an outer wall of the sheath body includes an inner layer comprising a first material, the inner layer defining the lumen, and an outer layer comprising a second material that is different from the first material.

In a thirteenth example relating to the device of the twelfth example, a coefficient of friction of the first material is lower than a coefficient of friction of the second material.

In a fourteenth example relating to the device of the twelfth example or the thirteenth example, the second material has at least one of a compressive strength, a yield strength, or a tensile strength that is greater than at least one of a corresponding compressive strength, a yield strength, or a tensile strength of the first material.

In a fifteenth example relating to the device of any of the twelfth through fourteenth examples, the first material comprises at least one of polytetrafluoroethylene (PTFE), high-density polyethylene (HDPE) or low-density polyethylene (LDPE).

In a sixteenth example relating to the device of any of the twelfth through fifteenth examples, the device further comprises a pharmacologically-active agent on an outer surface of the balloon or embedded in the balloon, wherein the first material is substantially chemically non-reactive with the pharmacologically-active agent.

In a seventeenth example relating to the device of the sixteenth example, the pharmacologically-active agent comprises at least one of an antiproliferative agent or an anti-restenotic agent.

In an eighteenth example relating to the device of any of the twelfth through seventeenth examples, the second material comprises at least one of a polyamide or a polyamide block copolymer.

In a nineteenth example relating to the device of any of the twelfth through eighteenth examples, the outer layer includes a visible marking indicative of a composition of the second material.

In a twentieth example relating to the device of any of the twelfth through nineteenth examples, the inner layer is about 10% to about 30% of a thickness of the outer wall of the sheath body.

In a twenty-first example relating to the device of any of the twelfth through twentieth examples, the outer layer is about 60% to about 90% of a thickness of the outer wall of the sheath body.

In a twenty-second example relating to the device of any of the twelfth through twenty-first examples, the outer wall of the sheath body further includes an intermediate layer positioned between the inner layer and the outer layer, the intermediate layer comprising a material configured to bond the inner layer to the outer layer.

In a twenty-third example relating to the device of the twenty-second example, the intermediate layer is about 5% to about 15% of a thickness of the outer wall of the sheath body.

In a twenty-fourth example relating to the device of any of the twelfth through twenty-third examples, a proximal portion of the catheter body extends proximally of the sheath when the expandable balloon is received within the lumen of the sheath body.

In a twenty-fifth example, aspects of the disclosure relate to a device including a catheter including a catheter body, an expandable balloon positioned on the catheter body, and a splittable sheath including a sheath body defining a lumen configured to receive the expandable balloon. An outer wall of the sheath body defines a groove extending longitudinally along an outer surface of the sheath body, the outer wall of the sheath body including: an inner layer comprising a first material, the inner layer defining the lumen; and an outer layer comprising a second material, wherein a coefficient of friction of the first material is lower than a coefficient of friction of the second material. The sheath further comprises a tab extending from a proximal end or a distal end of the sheath body, wherein outward movement of the tab relative to a central longitudinal axis of the sheath body causes splitting of the sheath body along the groove, and wherein the tab includes a major surface having an outer edge defining a serpentine shape.

In a twenty-sixth example relating to the device of the twenty-fifth example, a width of the tab is substantially the same as a width of the lumen of the sheath body, the width being measured in a direction perpendicular to the central longitudinal axis of the sheath body.

In a twenty-seventh example relating to the device of the twenty-fifth example or the twenty-sixth example, the tab is integrally formed with the sheath body.

In a twenty-eighth example relating to the device of any of the twenty-fifth through twenty-seventh examples, the tab comprises a first tab including a first major surface having a first outer edge defining a first serpentine shape, the device further comprising a second tab extending from the proximal end or the distal end of the sheath body, wherein outward movement of the second tab relative to the first tab causes splitting of the sheath body, the second tab including a second major surface having a second outer edge defining a second serpentine shape.

In a twenty-ninth example relating to the device of any of the twenty-fifth through twenty-eighth examples, the groove comprises a first groove, and the sheath body defines a second groove extending longitudinally along the outer surface of the sheath body, wherein outward movement of the tab relative to the central longitudinal axis of the sheath body causes splitting of the sheath body along the first and second grooves.

In a thirtieth example relating to the device of the twenty-ninth example, the first groove and the second groove are positioned on opposite sides of the central longitudinal axis of the sheath body.

In a thirty-first example relating to the device of any of the twenty-fifth through thirtieth examples, the groove is aligned with the outer edge of the tab along an axis parallel to the central longitudinal axis of the sheath body.

In a thirty-second example relating to the device of any of the twenty-fifth through thirty-first examples, the groove extends from the outer surface of the outer wall of the sheath body through about 50% to about 90% of a thickness of the outer wall of the sheath body.

In a thirty-third example relating to the device of any of the twenty-fifth through thirty-second examples, the groove extends along about 2% to about 20% of a perimeter of a cross-section of the sheath body taken orthogonal to the central longitudinal axis of the sheath body.

In a thirty-fourth example relating to the device of any of the twenty-fifth through thirty-third examples, the second material has at least one of a compressive strength, a yield strength, or a tensile strength that is greater than at least one of a corresponding compressive strength, a yield strength, or a tensile strength of the first material.

In a thirty-fifth example relating to the device of any of the twenty-fifth through thirty-fourth examples, the first material comprises at least one of polytetrafluoroethylene (PTFE), high-density polyethylene (HDPE) or low-density polyethylene (LDPE).

In a thirty-sixth example relating to the device of any of the twenty-fifth through thirty-fifth examples, the device further includes a pharmacologically-active agent on the outer surface of the balloon or embedded in the balloon, wherein the first material is substantially chemically non-reactive with the pharmacologically-active agent.

In a thirty-seventh example relating to the device of the thirty-sixth example, the pharmacologically-active agent comprises at least one of an antiproliferative agent or an anti-restenotic agent.

In a thirty-eighth example relating to the device of any of the twenty-fifth through thirty-seventh examples, the second material comprises at least one of a polyamide or a polyamide block copolymer.

In a thirty-ninth example relating to the device of any of the twenty-fifth through thirty-eighth examples, the outer layer includes a visible marking indicative of a composition of the second material.

In a fortieth example relating to the device of any of the twenty-fifth through thirty-ninth examples, the inner layer is about 10% to about 30% of a thickness of the outer wall of the sheath body.

In a forty-first example relating to the device of any of the twenty-fifth through fortieth examples, the outer layer is about 60% to about 90% of a thickness of the outer wall of the sheath body.

In a forty-second example relating to the device of any of the twenty-fifth through forty-first examples, the outer wall of the sheath body further includes an intermediate layer positioned between the inner layer and the outer layer, the intermediate layer comprising a material configured to bond the inner layer to the outer layer.

In a forty-third example relating to the device of any of the twenty-fifth through forty-second examples, the intermediate layer is about 5% to about 15% of a thickness of the outer wall of the sheath body.

In a forty-fourth example relating to the device of any of the twenty-fifth through forty-third examples, a proximal portion of the catheter body extends proximally of the sheath when the expandable balloon is received within the lumen of the sheath body.

In a forty-fifth example, aspects of the disclosure relate to a device that includes a catheter including a catheter body, and an expandable balloon positioned on the catheter body; and a splittable sheath including a sheath body defining a lumen configured to receive the expandable balloon. An outer wall of the sheath body defines a groove extending longitudinally along an outer surface of the sheath body, the outer wall of the sheath body including: an inner layer comprising a first material, the inner layer defining the lumen, an outer layer comprising a second material, wherein a coefficient of friction of the first material is lower than a coefficient of friction of the second material; and an intermediate layer positioned between the inner layer and the outer layer, the intermediate layer comprising a material configured to bond the inner layer to the outer layer. The sheath further comprises a first tab extending from a proximal end or a distal end of the sheath body, the first tab including a first major surface having a first outer edge defining a first serpentine shape, and a second tab extending from the proximal end or the distal end of the sheath body, wherein outward movement of the second tab relative to the first tab causes splitting of the sheath body along the groove, the second tab including a second major surface having a second outer edge defining a second serpentine shape.

In a forty-sixth example relating to the device of the forty-fifth example, at least one of a width of the first tab or a width of the second tab is substantially the same as a width of the lumen of the sheath body, the width being measured in a direction perpendicular to the central longitudinal axis of the sheath body.

In a forty-seventh example relating to the device of the forty-fifth or the forty-sixth example, at least one of the first tab or the second tab is integrally formed with the sheath body.

In a forty-eighth example relating to the device of any of the forty-fifth through forty-seventh examples, the groove comprises a first groove, and the sheath body defines a second groove extending longitudinally along the outer surface of the sheath body, wherein outward movement of the second tab relative to the first tab causes splitting of the sheath body along the first and second grooves.

In a forty-ninth example relating to the device of the forty-eighth example, the first groove and the second groove are positioned on opposite sides of the central longitudinal axis of the sheath body.

In a fiftieth example relating to the device of any of the forty-fifth through forty-ninth examples, the groove is aligned with at least one of the first outer edge of the first tab or the second outer edge of the second tab along an axis parallel to the central longitudinal axis of the sheath body.

In a fifty-first example relating to the device of any of the forty-fifth through fiftieth examples, the groove extends from the outer surface of the outer wall of the sheath body through about 50% to about 90% of a thickness of the outer wall of the sheath body.

In a fifty-second example relating to the device of any of the forty-fifth through fifty-first examples, the groove extends along about 2% to about 20% of a perimeter of a cross-section of the sheath body taken orthogonal to the central longitudinal axis of the sheath body.

In a fifty-third example relating to the device of any of the forty-fifth through fifty-second examples, the second material has at least one of a compressive strength, a yield strength, or a tensile strength that is greater than at least one of a corresponding compressive strength, a yield strength, or a tensile strength of the first material.

In a fifty-fourth example relating to the device of any of the forty-fifth through fifty-third examples, the first material comprises at least one of polytetrafluoroethylene (PTFE), high-density polyethylene (HDPE) or low-density polyethylene (LDPE).

In a fifty-fifth example relating to the device of any of the forty-fifth through fifty-fourth examples, the device further includes a pharmacologically-active agent on the outer surface of the balloon or embedded in the balloon, wherein the first material is substantially chemically non-reactive with the pharmacologically-active agent.

In a fifty-sixth example relating to the device of the fifty-fifth example, the pharmacologically-active agent comprises at least one of an antiproliferative agent or an anti-restenotic agent.

In a fifty-seventh example relating to the device of any of the forty-fifth through fifty-sixth examples, the second material comprises at least one of a polyamide or a polyamide block copolymer.

In a fifty-eighth example relating to the device of any of the forty-fifth through fifty-seventh examples, the outer layer includes a visible marking indicative of a composition of the second material.

In a fifty-ninth example relating to the device of any of the forty-fifth through fifty-eighth examples, the inner layer is about 10% to about 30% of a thickness of the outer wall of the sheath body.

In a sixtieth example relating to the device of any of the forty-fifth through fifty-ninth examples, the outer layer is about 60% to about 90% of a thickness of the outer wall of the sheath body.

In a sixty-first example relating to the device of any of the forty-fifth through sixtieth examples, the intermediate layer is about 5% to about 15% of a thickness of the outer wall of the sheath body.

In a sixty-second example relating to the device of any of the forty-fifth through sixty-first examples, a proximal portion of the catheter body extends proximally of the sheath when the expandable balloon is received within the lumen of the sheath body.

In a sixty-third example, aspects of the disclosure relate to a method that includes positioning a distal end of the splittable sheath of any of the first through the sixty-second examples adjacent a proximal end of an introducer, the introducer being introduced in vasculature of a patient; advancing the expandable balloon distally through the lumen of the sheath body and into an introducer lumen of the introducer; and after advancing the expandable balloon distally through the lumen of the sheath body and into the introducer lumen, splitting the sheath body, wherein splitting the sheath body includes moving the tab outward relative to the central longitudinal axis of the sheath body.

In a sixty-fourth example relating to the device of the sixty-third example, the method further includes advancing the catheter to a treatment site within the patient vasculature; and inflating the expandable balloon.

In a sixty-fifth example, aspects of the disclosure relate to a method that includes cutting an end portion of a sheath body to define a tab including a major surface having an outer edge defining a serpentine shape, the sheath body defining a lumen configured to receive an expandable balloon of a catheter, wherein cutting the end portion of the sheath body includes cutting a width of the sheath body sufficient to longitudinally slit the end portion of the sheath body.

In a sixty-sixth example relating to the device of the sixty-fourth example, cutting the end portion of the sheath body includes compressing the end portion, and stamping opposite edges of the compressed end portion to define the serpentine shape and longitudinally slit the end portion of the sheath body.

In a sixty-seventh example relating to the device of the sixty-fifth example or the sixty-sixth example, the method further includes forming a groove extending longitudinally along a length of the sheath body by at least one of laser cutting, mechanical cutting, or selective chemical dissolution.

In a sixty-eighth example relating to the device of any of the sixty-fifth through sixty-seventh examples, the method further includes introducing the expandable balloon positioned on a catheter body into the lumen of the sheath body to form a sheathed catheter assembly; and sterilizing the sheathed catheter assembly.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a side view of an example device including a splittable sheath and catheter including expandable balloon positioned on a catheter body and received within a lumen of the splittable sheath.

FIG. 2 is a cross-sectional view of the catheter of FIG. 1, where the cross-section is taken along a plane A-A orthogonal to a longitudinal axis of the catheter.

FIG. 3 is a side view of the catheter of FIG. 1, where the expandable balloon is positioned on the catheter body in a collapsed configuration.

FIG. 4A is a perspective view of an example splittable sheath including a first tab and a second tab, where an outer edge of a major surface of the first tab and an outer edge of a major surface of the second tab each have a serpentine shape.

FIG. 4B is a side view of the splittable sheath of FIG. 4A.

FIG. 5A is a perspective view of another example splittable sheath, where a sheath body of the sheath includes an outer wall having an inner layer and an outer layer.

FIG. 5B is a side view of the splittable sheath of FIG. 5A.

FIG. 5C is another side view of the splittable sheath of FIG. 5A.

FIG. 5D is a cross-sectional view of the splittable sheath of FIG. 5A, where the cross-section is taken along a plane C-C orthogonal to a longitudinal axis of the sheath.

FIG. 7A is a side view of another example splittable sheath including a first groove and a second groove extending longitudinally along an outer surface of a body of the sheath.

FIG. 11 is a side view of another example splittable sheath including a first tab and a second tab, and illustrates another example serpentine shape for an outer edge of a major surface of the first tab and an outer edge of a major surface of the second tab.

FIG. 12 is a side view of another example splittable sheath including a first tab and a second tab, and illustrates another example serpentine shape for an outer edge of a major surface of the first tab and an outer edge of a major surface of the second tab.

Figure 4C:
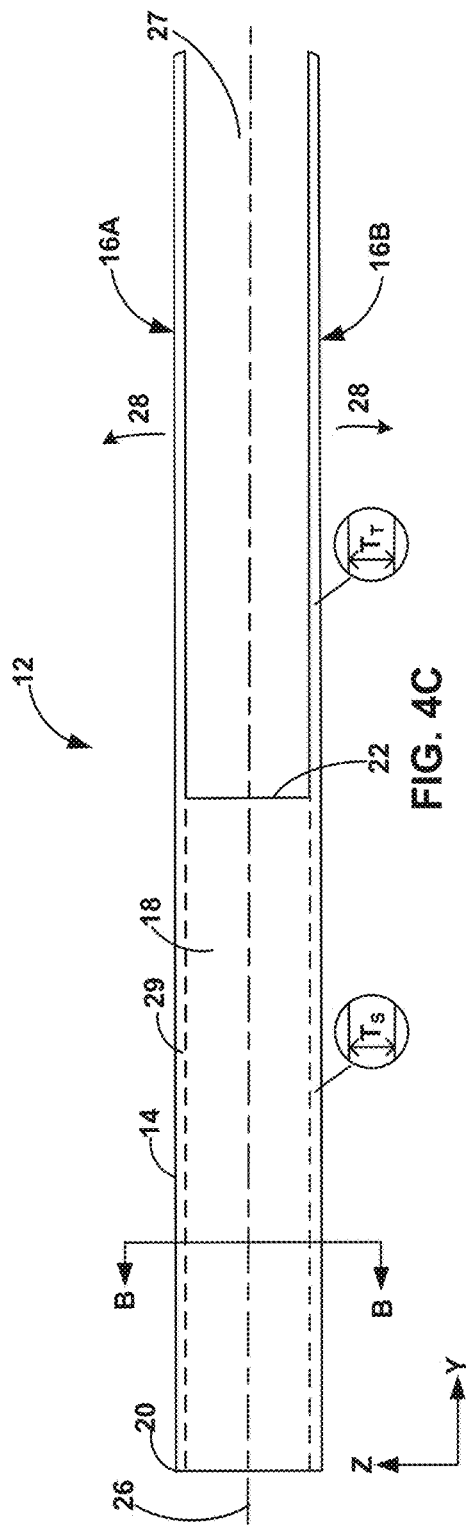
FIG. 4C is another side view of the splittable sheath of FIG. 4A.

The details of one or more examples of this disclosure are set forth in the accompanying drawings and the description below. Other features, objects, and advantages of this disclosure will be apparent from the description and drawings, and from the claims.

DETAILED DESCRIPTION

Conditions related to the narrowing of blood vessels within the human body affect millions of people worldwide. In some cases, narrowing of a blood vessel can be caused by a buildup of plaque within the lumen of the vessel or within the vessel wall (atherosclerosis). Atherosclerosis may occur in portions of the vasculature that supply the heart, brain, and other regions of the body including the limbs. If not treated, the reduction in blood flow caused by atherosclerosis can lead to heart attack, stroke, tissue death in the extremities, and other adverse outcomes. Options for restoring adequate blood flow in a vessel affected by atherosclerosis include angioplasty procedures, which may include the delivery of expandable balloons, stents and/or drugs to the vessel.

In some examples, angioplasty procedures for restoring blood flow to an affected vessel may include inflating an expandable balloon within the affected vessel to compress accumulated plaque against the vessel wall. For example, a clinician may introduce a catheter having an expandable balloon into the vasculature of a patient via an introducer sheath placed in a small incision in the patient's skin. The clinician then may advance the catheter to a treatment site in the target vessel, and inflate the expandable balloon via an inflation lumen within the catheter. In some examples, an expandable balloon may be coated with or otherwise carry a pharmacologically-active agent, such as an anticoagulant, anti-inflammatory agent, antiproliferative, or other drug. This may be referred to as a drug-coated balloon. The pharmacologically-active agent may be transferred from an outer surface of the expandable balloon to the tissue of the target vessel when the expandable balloon is inflated and contacts the tissue. In this manner, drug-coated balloons may provide added clinical benefit to angioplasty procedures by delivering pharmacologically-active agents directly to the affected vessel, and thereby reducing the likelihood of vessel re-stenosis.

In some cases, it may be beneficial to protect a balloon of a catheter following manufacture and prior to introduction into a body of a patient. For example, the balloon may be subject to kinking, stretching, or self-adhesion of balloon components during packaging, shipping, storage, or handling. With some drug-coated balloons, a drug coating on an outer surface of the balloon may be eroded after manufacture and prior to use of the balloon during the packaging, shipping, storage, or handling of the balloon prior to being introduced. A protective sheath positioned at least partially over the balloon may help maintain the structural integrity of the balloon, the integrity of the drug coating, or the structural integrity of both the balloon and the drug coating.

In some examples, a protective balloon sheath may be applied at least partially over the balloon following manufacture and assembly of the balloon catheter, but prior to packaging of the balloon catheter. Such balloon sheaths may help protect the structural integrity of the balloon and any drug coatings thereon by shielding the balloon from direct physical contact with the external environment prior to introduction of the balloon into a patient's body. For example, the balloon sheath may enable a clinician to avoid handling the balloon directly. Instead, the clinician may attach the balloon sheath to an introducer sheath, and advance the balloon through the balloon sheath, through the introducer sheath, and into the vasculature of the patient by manipulating a catheter body of the balloon catheter.

A balloon sheath may be a tubular structure that is configured to be positioned around a catheter body. In example medical devices having a balloon sheath that is not configured to be easily removable from over a catheter, a portion of the catheter equal to a length of a body of the sheath may be operationally unusable, as the sheath may not be slidable proximally over a manifold or other hub at a proximal end of the catheter or distally into an introducer sheath used to aid introduction of the balloon catheter into vasculature of a patient. In such example medical devices, a length of a catheter may need to be increased to account for an operationally unusable length of the catheter, thereby increasing the amount of material needed to manufacture the catheter and increasing the overall length of the catheter. Removing a balloon sheath from around a catheter may enable substantially an entire length of a catheter body to be operationally usable, including a length of the catheter body housed within the balloon sheath when an expandable balloon is received within a lumen of the balloon sheath. While a clinician may cut the balloon sheath off the catheter, cutting the balloon sheath off the catheter may require an additional cutting tool, as well as additional time during a medical procedure, which can be undesirable. Further, a cutting tool may be relatively sharp, and use of the tool in such close proximity to the catheter body may be undesirable.

In examples described herein, a balloon sheath is configured to be split longitudinally and removed from a balloon catheter. The balloon sheath may be referred to as a splittable balloon sheath or a splittable sheath. These exemplary splittable sheaths may be split and removed from the catheter without the aid of a sharp cutting tool. A splittable sheath may include one or more tabs configured to be grasped by a clinician and moved relative to a longitudinal axis of a sheath body of the sheath to cause splitting of the balloon sheath into multiple portions. A clinician may manually grasp the one or more tabs or may grasp the one or more tabs with a gripping tool that grips onto the one or more tabs.

In some examples, the tabs of a splittable sheath may have a texturized major surface (e.g., having ridges, bumps, or the like) configured to facilitate gripping of the tabs by a clinician during splitting and removal of the sheath. However, in such examples, the texturized major surface of the tabs may limit the efficacy of pre-packaging cleaning and sterilization of the sheath. For example, the texture may inhibit the pre-sterilization cleaning of the sheath by making the space between the ridges, bumps, or other textural features difficult to access with mechanical or chemical cleaning implements. As a result, contaminants may remain trapped among the textural features of such sheath tabs even after cleaning. Lingering contaminants among the textural features of the sheath tabs during subsequent sterilization procedures may shield microorganisms and infectious particles from destruction by a sterilant, thereby potentially limiting the efficacy of sterilization procedures.

This disclosure describes examples of splittable sheaths having tabs that include features that facilitate gripping by a clinician without adversely affecting the efficacy of pre-packaging cleaning and sterilization of the sheath in the same way that the textured major surface limits the packaging cleaning and sterilization. The example splittable sheaths described herein may include one or more tabs that include a major surface having an outer edge that defines a particular shape, such as a serpentine shape, which is further described below, that is configured to aid gripping of the tab by a clinician. The shape of the outer edge of the major surface of the tab may provide a gripping surface for the clinician's fingers or a gripping tool as the clinician moves the tab to split the sheath and remove the sheath from the catheter. In this way, the one or more tabs of a splittable sheath described herein may aid the removal of the balloon sheath from a catheter. In addition, the shape of the outer edges may enable mechanical and chemical cleaning implements to relatively easily access the outer edges of the tabs prior to sterilization and packaging of the sheath.

Also described herein are methods of using devices that comprise a balloon catheter and a splittable sheath, as well as methods of manufacturing the same. In some examples, methods of manufacturing the splittable sheaths described in this disclosure may provide the advantages of simplified manufacturing relative to other example splittable sheaths. For example, the tabs of the splittable sheaths described herein may be defined by shearing off a relatively small amount of material from a portion of the sheath, leaving the sheath ready to be assembled over a balloon catheter with minimal to no further processing of the tabs.

While the present disclosure describes devices including balloon catheters and splittable sheaths primarily in the context of angioplasty procedures for treating atherosclerosis, the devices of the present disclosure may also be used for restoring patency to other lumens within the body of a patient, such as a lumen of a fallopian tube, urethra, esophagus, bile duct, or other anatomical structure. Further, the splittable sheaths described herein may be used with medical device other than balloon catheters, such as self-expandable stent delivery systems, atherectomy devices, or other devices in which a bypass of a hemostatic valve present on an outer sheath of the device or another large structure present on the outer sheath is desirable.

FIGS. 1-3 illustrate an example medical device 10 that may be used alone or in conjunction with other medical devices, such as introducer sheaths. FIG. 1 is a side view of the medical device 10, which is configured for use in a medical procedure to restore adequate blood flow to a target vessel within the body of a patient. The medical device 10 includes a splittable sheath 12 and a catheter 30 including an expandable balloon 50. The splittable sheath 12 includes a sheath body 14, a first tab 16A, and a second tab 16B. The sheath body 14 defines a lumen 18 having a length 24 (the length 24 being measured along a longitudinal axis 40 of the device 10) that is configured to receive the expandable balloon 50 having a length 52 (also measured along the longitudinal axis 52 of the device 10). The body 14 of the splittable sheath 12 includes a distal end 20 and a proximal end 22, with the first tab 16A and the second tab 16B extending proximally from the proximal end 22. In other examples, the first tab 16A and the second tab 16B may extend in a distal direction from the distal end 20. The catheter 30 includes a catheter body 32 having a proximal end 34, and a hub 36 positioned at the proximal end 34 of the catheter body 32.

The expandable balloon 50 is carried by the catheter body 32 of the catheter 30, and can be positioned at any suitable longitudinal position along the catheter body 32. In the example shown in FIG. 1, the expandable balloon 50 is positioned at a distal portion of the catheter body 32. In some examples, the expandable balloon 50 is fixedly attached to the catheter body 32, such as by adhesives, solder, welding, or other suitable fixation mechanisms, so that the expandable balloon 50 may remain securely attached to the catheter body 32 when the expandable balloon 50 is inflated at the target site.

In some examples, the lumen 18 of the sheath body 14 of the splittable sheath 12 may be sized to substantially enclose the expandable balloon 50 while enabling the expandable balloon 50 to be longitudinally moveable within the lumen 18. For example, a greatest cross-sectional dimension (e.g., a diameter) of the lumen 18 may be equal to or larger than a greatest cross-sectional dimension (e.g., a diameter) of the expandable balloon 50 in an unexpanded configuration. In some such examples, the cross-sectional dimension of the lumen 18 may be sufficiently larger than the cross-sectional dimension of the expandable balloon 50 to enable the expandable balloon 50 to be readily slidable within the lumen 18 when a clinician moves the catheter 30 proximally or distally relative to the splittable sheath 12, such that the integrity of a drug coating that may be included on the expandable balloon 50 may be substantially maintained while the expandable balloon 50 is received within the lumen 18.

In some examples, the sheath body 14 may include a lubricious material along the lumen 18, the lubricious material being configured to reduce friction between the balloon 50 and the inner surface of the sheath body 14 defining the lumen 18. For example, the lumen 18 may be coated with a material having a relatively low coefficient of friction, or a material of the sheath body 14 may have a relatively low coefficient of friction. Such materials, (e.g., polytetrafluoroethylene (PTFE) or the like), may help preserve the integrity of a drug coating that may be included on the expandable balloon 50. Reducing the friction between the inner surface of the sheath body 14 defining the lumen 18 and the balloon 50 may help substantially maintain the integrity of a drug coating that may be included on the outer surface of the expandable balloon 50 by at least reducing the amount of drug coating that is inadvertently removed by the sheath body 14.

In some examples, the length 24 of the lumen 18 may be sufficient to enclose at least a majority of a length 52 of the expandable balloon 50, such as about 100% of the length 52 of the balloon 50, or about 60% to about 95% of the length 52 of the expandable balloon 50. In addition, in some examples, the length 24 of the lumen 18 may be sufficient to fully enclose the length 52 of the expandable balloon 50, such that the length 24 may be about 100% to about 125% of the length 52 of the expandable balloon 50. Configuring the splittable sheath 12 to substantially enclose the length 52 of the expandable balloon 50 while also enabling the expandable balloon 50 to be longitudinally moveable within the lumen 18 may help prevent a clinician or other use from inadvertently contacting the expandable balloon 50 prior to introduction of the expandable balloon 50 into the vasculature of a patient.

The splittable sheath 12 is configured to contain the expandable balloon 50 within the lumen 18 until the expandable balloon 50 is advanced out of the lumen 18. A clinician may, for example, advance the balloon 50 (and the catheter body 32) distally until the balloon 50 exits the lumen 18 and enters the vasculature of a patient, or, in some examples, into an introducer sheath that has been inserted into the vasculature of the patient through the patient's skin.

In some cases, it may be advantageous to retain the splittable sheath 12 on the catheter body 32 and over the balloon 50 until the balloon 50 has been advanced out of the lumen 18, e.g., into an introducer sheath or the vasculature of a patient. For example, retaining the splittable sheath 12 on the catheter body 32 until the expandable balloon 50 has been advanced distally into an introducer sheath or the vasculature of a patient may help protect the structural integrity of the expandable balloon 50 and any drug coatings thereon by shielding the expandable balloon 50 from direct physical contact with the external environment prior to introduction of the expandable balloon 50 into the patient's body. In some examples, the splittable sheath 12 also may serve to stabilize and guide the expandable balloon 50 as it is being advanced into an introducer sheath or into the patient's body. Thereafter, it may be advantageous to remove the splittable sheath 12 from the catheter body 32, to enable an entire length of the catheter body 32 to be advanced through an introducer sheath or directly into the patient vasculature. In other examples, the splittable sheath 12 may be removed from the catheter body 32 prior to introduction of the expandable balloon 50 into the patient's body, or may be retained on the catheter body 32 after the expandable balloon has been introduced into the patient's body.

The first tab 16A and the second tab 16B of the splittable sheath 12 enable splitting of the splittable sheath 12 into multiple portions, such that the splittable sheath 12 may be easily removed from over the catheter 30. For example, the first tab 16A and the second tab 16B may be configured to enable the splittable sheath 12 to be divided into two portions when a clinician moves the tabs 16A, 16B outward with respect to the longitudinal axis 40. The tabs 16A, 16B are each mechanically connected to (e.g., attached to or integral with) the sheath body 14, such that as the tabs 16A, 16B are moved outward with respect to the longitudinal axis 40, the sheath body 14 also moves with the tabs 16A, 16B and divides in a longitudinal direction into at least two different portions. The two different portions can be, for example, longitudinal halves of sheath body 14. The longitudinal direction is measured in the y-axis direction, where orthogonal x-y axes are shown in FIG. 1, and other orthogonal axes are shown in the other figures, for ease of description only. Further, the orthogonal x-y-z axes shown in the figures provide a common frame of reference for the different views of the devices described herein.

In some cases, it may be advantageous for a clinician to be able to split the balloon sheath 12 and remove the sheath 12 from over a catheter 30 during a procedure to advance the expandable balloon 50 to a target site within the vasculature. For example, configuring the splittable sheath 12 to be removable from over the catheter 30 may enable a clinician to advance a greater portion of a length of the catheter 30 into the vasculature of the patient than would be practicable if the sheath 12 were not easily removeable from the catheter 30, or at least minimize the length of the catheter body 32 needed for a medical procedure. As discussed above, in example medical devices having a balloon sheath that is not configured to be removable from over a catheter, a portion of the catheter equal to a length of a body of the balloon sheath may be operationally unusable in order to accommodate the placement of the balloon sheath over the catheter body, even after the balloon sheath is no longer positioned over the balloon of the catheter. Thus, the splitting and removal from a catheter of the splittable sheaths described herein, such as the splittable sheath 12, may enable substantially an entire length of the catheter body 32 to be operationally usable, including a length of the catheter body 32 housed within the splittable sheath 12 when the expandable balloon 50 is received within the lumen 18.

FIG. 2 is a cross-sectional view of the catheter 30 taken along the line A-A in FIG. 1, which extends orthogonally to the longitudinal axis 40 of the device 10. As shown in FIG. 2, the catheter 30 includes an inflation lumen 44. The catheter 30 may also include a guidewire lumen 42 configured to receive a guidewire 38. During use of the medical device 10, the guidewire 38 may be introduced into the vasculature of a patient, and then the catheter body 32 may be navigated over the guidewire 38 to the target site.

In some examples, the guidewire lumen 42 may extend longitudinally through the catheter 30 from a distal portion of the catheter body 32 to the hub 36 positioned at the proximal end 34 of the catheter 30. The hub 36 may include a first port that provides access to the guidewire lumen 42 to enable a clinician to advance the catheter body 32 along the guidewire 38. Similarly, the inflation lumen 44 may extend longitudinally through the catheter 30 from the hub 36 to the expandable balloon 50. The hub 36 may include a second port that provides access to the inflation lumen 44. In some examples, the inflation lumen 44 terminates distally at an opening to the interior of the expandable balloon 50. The inflation lumen 44 may be configured to receive a fluid that is introduced into the inflation lumen 44 from the hub 36 to expand or inflate the expandable balloon 50 (e.g., once the expandable balloon 50 has been navigated to the target site).

FIG. 3 is a side view of the catheter 30 with the splittable sheath 12 removed from around the expandable balloon 50, and illustrates the expandable balloon 50 positioned on the catheter body 32 in an unexpanded condition. In some examples, the expandable balloon 50 includes a coating on an external surface 51 of the expandable balloon. As depicted in FIG. 3, the expandable balloon 50 is in a deflated state, and is folded or rolled into a physically smaller profile (e.g., smaller than an inflated state of the expandable balloon 50). The general shape of the deflated state of the expandable balloon 50 shown in FIG. 3 is for illustration purposes only; other shapes and configurations of the expandable balloon 50 in a deflated state are also possible. Further, as depicted in FIG. 3, the guidewire 38 may extend through the guidewire lumen 42 of the catheter body 32, from a position distal to the expandable balloon 50 longitudinally through the catheter 30 to the hub 36.

The expandable balloon 50 may be formed from any suitable material that provides sufficient strength and flexibility for the pressures experienced by the expandable balloon 50 during the inflation procedure and during a medical procedure. The materials from which the expandable balloon 50 is formed may be biocompatible and compatible (i.e., chemically non-reactive) with a drug coating on an external surface 51 of the expandable balloon 50. In some examples, materials from which the expandable balloon 50 is formed may include nylon, polyethylene terephthalate (PET), polyethylene (such as crosslinked polyethylene), polyurethane, polyvinyl chloride, silicone elastomer, or the like.

The coating on the external surface 51 of the balloon 50 may be any suitable coating that facilitates use of balloon 50, a medical procedure, or the like. In some examples, the coating may include, for example, a lubricious coating (either hydrophilic or hydrophobic), a drug coating, or the like. In some examples, the drug coating may include a pharmacologically-active agent selected to treat vascular disease, such as an anticoagulant, anti-inflammatory agent, antiproliferative, or other agent or drug. For example, the anti-proliferative drug paclitaxel may be used in coronary angioplasty procedures to help reduce unwanted cell growth. In some examples, the drug coating may further include an excipient to facilitate release of the drug from the drug coating. Example excipients include urea, polysorbate, sorbitol, or other suitable agents.

FIGS. 4A-4C illustrate an example of the splittable sheath 12 of the medical device 10 of FIGS. 1-3. FIG. 4A is a perspective view of the splittable sheath 12, FIG. 4B is a side view of the splittable sheath 12, and FIG. 4C is another side view of the splittable sheath 12 rotated approximately 90 degrees from the view of FIG. 4B. The splittable sheath 12 may be made by any suitable technique, such as by molding or extrusion of any suitable materials, such as, but not limited to, a polyamide or a polyamide block copolymer (e.g., PEBAX or other member of the PEBA family). The material and configuration of the splittable sheath 12 may have sufficient stiffness to resist kinking or excessive bending as the expandable balloon 50 and the catheter 30 are advanced through the lumen 18 of the splittable sheath 12, but nonetheless pliable enough to be torn when the first tab 16A and the second tab 16B are grasped by a clinician and moved outward relative to a central longitudinal axis 26 of the sheath body 14, which may be co-axial with the central longitudinal axis 40 of the device 10 in some examples.

As the clinician moves the tabs 16A, 16B in the outward direction 28 (shown in FIG. 4C) away from the central longitudinal axis 26, and, in some examples, also in a distal direction, the sheath body 14 divides into at least a first portion including the tab 16A and a second portion including the tab 16B. The at least two portions may be completely separate from each other, or may be mechanically connected to each other at an end portion of the sheath body 14. In some examples in which the at least two portions remain mechanically connected together, the mechanical connection may be configured a clinician may pull the at least two portions apart to fully separate them from each other without the aid of a cutting tool.

In the example shown in FIGS. 4A-4C, the first tab 16A and the second tab 16B extend proximally from the proximal end 22 of the sheath body 14. In such examples, a split in the sheath body 14 will form and lengthen in a proximal-to-distal direction (i.e., from the proximal end 22 of the sheath body toward the distal end 20 of the sheath body) as the clinician continues to move the tabs 16A, 16B in an outward direction, away from central longitudinal axis 26. In other examples (not shown), the first tab 16A and the second tab 16B may extend distally from the distal end 20 of the sheath body 14. In such examples, a clinician may grasp the tabs 16A, 16B and split the splittable sheath 12 in much the same manner as examples in which the tabs 16A, 16B extend proximally from the proximal end 22 of the sheath body 14. That is, in such examples, the clinician may move the tabs 16A, 16B outwardly with respect to the central longitudinal axis 26 of the sheath body 14, although the split in the sheath body 14 would form and lengthen in a distal-to-proximal direction as the clinician continues to move the tabs 16A, 16B. As the clinician moves the tabs 16A, 16B in the outward direction away from central longitudinal axis 26, the tabs 16A, 16B may also be moved in a proximal direction to facilitate the splitting of the sheath body 14 into at least two portions.

Although the splittable sheath 12 shown in FIGS. 4A-4C includes the two tabs 16A, 16B, in other examples, the splittable sheath 12 may include a single tab (e.g., only one of the tabs 16A or 16B) or more than two tabs, which may extend from either the distal end 20 or the proximal end 22 of the sheath body 14. In examples in which only a single tab extends from sheath body 14, the clinician may grasp the tab with one hand (or tool) and grasp the sheath body 14 with the other hand (or a tool) and hold the sheath body 14 stationary while moving the tab outwardly with respect to the central longitudinal axis 26, thereby causing the sheath body 14 to longitudinally split into multiple portions that can be more easily removed from over the catheter 30 than the unsplit sheath body 14.

The sheath body 14 includes an outer wall 29 defining the inner lumen 18 that is configured to receive the balloon 50. In some examples, the first tab 16A and the second tab 16B may be formed integrally with the sheath body 14, such that both the outer wall 29 of the sheath body 14 and the tabs 16A, 16B are manufactured from a single piece of material. In these examples, the tabs 16A, 16B may be extensions of the outer wall 29, but are also movable relative to each other in the z-axis direction. For example, the tabs 16A, 16B may be formed by stamping a portion of the splittable sheath 12 to define the shape of the tabs 16A, 16B and divide the sheath 12 into separate tabs 16A, 16B, as described below in further detail with respect to FIGS. 15 and 16A-16E. In other examples, first tab 16A and the second tab 16B may be formed separately from the sheath body 14 and mechanically connected to the sheath body 14 using any suitable technique, such as, but not limited to, an adhesive, chemical welding, ultrasonic welding, or another suitable chemical or mechanical connection mechanism.

In some examples, a greatest width $W_T$ (measured perpendicular to the central longitudinal axis 26 of the sheath body 14 and in the x-axis direction shown in FIG. 4B) of the tabs 16A, 16B may be less than or substantially equal to a greatest dimension $W_S$ of the lumen 18 (e.g., a diameter of the lumen 18, also measured perpendicular to the central longitudinal axis 26 of the sheath body 14) of the sheath body 14, as shown in FIG. 4B. In other examples, the greatest width $W_T$ of the tabs 16A, 16B may be greater than the greatest dimension $W_S$ of the lumen 18 of the sheath body 14, such as examples in which the tabs 16A, 16B are formed separately from the sheath body 14, or examples in which a tube from which the splittable sheath 12 is manufactured is wider at one end. In examples in which the greatest width $W_T$ is substantially equal to, or greater than, the greatest dimension $W_S$ of the lumen 18, the relatively larger surface area of the tabs 16A, 16B may provide enhanced gripability of the tabs 16A, 16B compared to examples in which the greatest width $W_T$ is less than the greatest dimension $W_S$ of the lumen 18, by maximizing the available gripping surface.

Tabs 16A, 16B may have any suitable length for aiding splitting of sheath body 14, the length being measured parallel to the central longitudinal axis 26 of the sheath body 14 (in the y-axis direction). For example, the tabs 16A, 16B may each may have a length of approximately about 20% to about 70% of a total length of the splittable sheath 12, such as about 50% of the length of the sheath 12. For example, a total length of the splittable sheath may be about 20 millimeters (mm) to about 300 mm, such that the tabs 16A, 16B each may have a length of about 4 mm to about 210 mm, such as about 20 mm to about 50 mm, depending on the relative proportions of the tabs 16A, 16B and the sheath body 14.

The first tab 16A and the second tab 16B respectively include a first major surface 17A and a second major surface 17B, which are surfaces that define the greatest continuous surface area of the tabs 16A, 16B. In the example shown in FIGS. 4A-4C, the major surfaces 17A, 17B extend generally in the x-y plane. Major surfaces 17A, 17B may be planar or nearly planar in some examples, and may be non-planar in other examples. For example, in examples in which tabs 16A, 16B are formed from the same tube as sheath body 12, the major surface 17A, 17B may be curved in the x-z plane, e.g., such that the concave surfaces of tabs 16A, 16B face each other. In other examples, the major surface 17A, 17B may be curved in the x-z plane such that the concave surfaces of tabs 16A, 16B face in opposite directions.

The first major surface 17A of the first tab 16A defines a first outer edge 19A, and the second major surface 17B of the second tab 16B defines a second outer edge 19B. As shown in FIG. 4A, the first outer edge 19A and the second outer edge 19B each have a serpentine shape. The serpentine shape may be defined by a winding, undulating, or otherwise nonlinear outer perimeter. In the illustrated example, the serpentine shape of the outer edges 19A, 19B is a wavy shape that forms interconnected "S" shapes or "C" shapes, although in some examples the serpentine shape of the outer edges 19A, 19B may form interconnected "U" shapes or other curvilinear or non-curvilinear shapes (e.g., a toothed shape). Other example serpentine shapes are described with reference to FIGS. 9-12.

In the example serpentine shapes shown in FIGS. 4A and 4B, the first outer edge 19A includes outwardly-curving portions 23A and the outer edge 19B includes outwardly-curving portions 23B, each of which arc outwardly relative to the central longitudinal axis 26 of the sheath body 14. Although the outer edges 19A, 19B are illustrated in FIG. 4A respectively as having four of the outwardly-curving portions 23A and four of the outwardly-curving portions 23B, the outer edges 19A, 19B may include a greater or lesser number of the outwardly-curving portions 23A, 23B in other examples. In examples in which the edges 19A, 19B include a greater number of the outwardly-curving portions 23A, 23B, for a given tab length, each of the outwardly-curving portions 23A, 23B may have a relatively smaller arc (e.g., greater radius of curvature) than examples in which the edges 19A, 19B include a lesser number of the outwardly-curving portions 23A, 23B. In examples in which the arcs of the outwardly-curving portions 23A, 23B are relatively smaller, the outer edges 19A, 19B may have a greater surface area, which in turn may provide increased gripability of the tabs 16A, 16B. In other examples, the relative arc size of the outwardly-curving portions 23A, 23B may stay substantially the same as the number of the outwardly-curving portions 23A, 23B changes, although a length of the tabs 16A, 16B may vary.

As shown in FIG. 4B, the serpentine shape of the first outer edge 19A of the first major surface 17A of the first tab 16A extends around an outer perimeter of the first tab 16A. In other examples, however, the serpentine shape may only extend around part of the first tab 16A, such as along only one side of longitudinal axis 26.

The serpentine shape of the first outer edge 19A and the second outer edge 19B provides a gripping surface for a clinician during splitting of the splittable sheath 12, while contributing to the accessibility of the tabs 16A, 16B to cleaning agents and sterilants used during manufacturing. The serpentine shape of the outer edges 19A, 19B may enable mechanical and chemical cleaning implements to access the outer edges 19A, 19B of the tabs 16A, 16B prior to sterilization and packaging of the splittable sheath 12, such as during the manufacturing process or prior to use. In addition, the serpentine shape of the outer edges 19A, 19B provides the tabs 16A, 16B with gripping surfaces while the major surfaces 17A, 17B may be substantially smooth (e.g., without textural features thereon). As described above, textural features on a major surface of a tab of a splittable sheath may inhibit a pre-sterilization cleaning of the sheath by making the space between the textural features difficult to access with mechanical or chemical cleaning implements. Thus, the relatively smoothness of the major surfaces 17A, 17B of the tabs 16A, 16B compared to the textured major surfaces of other tabs would enable mechanical and chemical cleaning implements to relatively easily access the major surfaces 17A, 17B prior to sterilization and packaging of the splittable sheath 12.

Major surfaces 17A, 17B are relatively smooth, e.g., without any textural design features (except for perhaps some inadvertent texture due to manufacturing techniques), or may have some features configured to aid gripping of tabs 16A, 16B, respectively. For example, at least one of the major surfaces 17A, 17B may include a ridge, a bump, or the like that protrudes from the outer surface of the tab 16A, 16B in a z-axis direction. This type of protrusion may help the clinician's finger or tool from slipping away from the tabs 16A, 16B. The one or more protrusions can extend from the outer surface of the tabs 16A, 16B, e.g., the surface of the tabs 16A, 16B that does not face the other tab, or can extend from the inner surface of the tabs 16A, 16B. In some examples, the major surfaces 17A, 17B only include a single protrusion or only two protrusions. In contrast to balloon sheaths that include tabs that includes textural features configured to aid gripping of the tabs, tabs 16A, 16B, even in examples that include one or more protrusions, include fewer and larger surface protrusions that do not interfere with cleaning of the tabs 16A, 16B, and the surface protrusions may be spaced further apart that the textural features of other tabs.

In some examples, one or both of the major surfaces 17A, 17B may define one or more openings therein, which may extend through an entirety of a thickness of the tabs 16A, 16B. The openings can help the clinician's finger or tool from slipping away from the tabs 16A, 16B, by providing a gripping surface.

The serpentine shape of the outer edges 19A, 19B provides a gripping surface for the clinician's fingers or tools as the clinician grasps the tabs 16A, 16B, thereby improving the security of a grip of the clinician's hands or tools on the tabs 16A, 16B while the clinician pulls the tabs 16A, 16B apart while splitting the splittable sheath 12. For example, the texture or bulk of some surgical gloves may hinder a clinician's ability to securely grasp objects such as the tabs of a splittable sheath. If a clinician senses that his or her grip on the tabs is not secure (e.g., his or her fingers or tool begin to slip), the clinician may be inclined to exert an excessive amount of force on the sheath in an attempt to obtain a secure grip on the tabs, which may result in a sudden splitting of the sheath and an unintended transfer of force to other portions of a medical device. Similar issues also may arise when a clinician uses a tool to grasp the tabs of a sheath, such as in examples in which the surface area of the tabs is limited. In the event of such an unintended transfer of force, portions of a medical device, such as an introducer sheath or a guidewire, may become shifted out of position and require repositioning, thereby increasing the time needed to complete the medical procedure. The serpentine shape of the outer edges 19A, 19B of the sheath 12 provides the clinician with greater control over the splittable sheath 12 by increasing a surface area of the outer edges 19A, 19B of the tabs, which helps enable the clinician to obtain a secure grip on the tabs 16A, 16B, and may reduce the likelihood of unintended transfers of force to other components of the medical device 10 or to a patient's body.

The side view of FIG. 4C shows the splittable sheath 12 rotated approximately 90° about the central longitudinal axis 26 of the sheath body 14 from the view shown in FIG. 4B. The tabs 16A, 16B can be seen in profile in FIG. 4C, with a space 27 between the tabs 16A, 16B that is approximately coextensive with the lumen 18. Due to the perspective of FIG. 4C, the serpentine shape of the outer edges 19A, 19B is not visible from this perspective. In some examples, due at least in part to the space 27 between the tabs 16A, 16B and the thicknesses $T_T$ of the tabs 16A, 16B, the tabs 16A, 16B are movable relative to each other in at least the z-axis direction.

In some examples, the thickness $T_T$ of each of the tabs 16A, 16B may be substantially similar to (e.g., equal to or nearly equal to) a thickness $T_S$ of the outer wall 29 of the sheath body 14. In these examples, the greatest distance between the tabs 16A, 16B (as defined by the space 27) may be substantially equal to the greatest dimension of the lumen 18 defined by sheath body 14, particularly in examples where the tabs 16A, 16B have been substantially flattened (i.e., without any curvature). In other examples, however, the thickness $T_T$ of each of the tabs 16A, 16B may be greater than a thickness $T_S$ of the outer wall 29 of the sheath body 14, which may further facilitate splitting of sheath body 14, or may be less than a thickness $T_S$ of the outer wall 29 of the sheath body 14. In these examples, the greatest distance between the tabs 16A, 16B in a resting state of sheath 12 in which no outer forces are applied to sheath 12 may be different than the greatest dimension of the inner lumen 18.

Figure 4D:
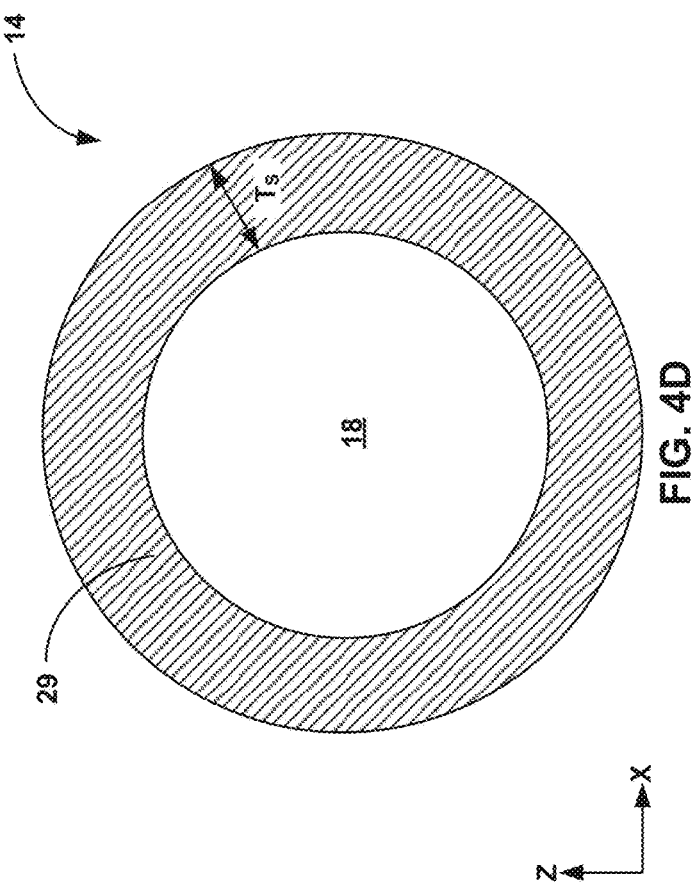
FIG. 4D is a cross-sectional view of the splittable sheath of FIG. 4A, where the cross-section is taken along a plane B-B orthogonal to a longitudinal axis of the sheath.

FIG. 4D is a cross-sectional view of the splittable sheath 12 of the device 10 of FIGS. 1-4C, the cross-section taken along line B-B in FIG. 4C, which extends orthogonal to the central longitudinal axis 26 of the sheath body 14. The perspective provided by the cross-section of FIG. 4D faces distally toward the distal end 20 of the sheath body 14. In the example shown in FIG. 4D, the outer wall 29 of the sheath body 14 includes a single layer of material, which may be any suitable material, such as, but not limited to a polymer. In some examples, the material of both the outer wall 29 and the tabs 16A, 16B may be a material of the amide family, such as a polyamide or a polyamide block copolymer (e.g., PEBAX or other member of the PEBA family).

In the example of FIG. 4D, the material and a thickness $T_S$ of the outer wall 29 may be selected to provide adequate stiffness to the sheath body 14. In some examples, the thickness $T_S$ of the outer wall 29 may be from about 0.10 mm to about 0.60 mm. In some examples, the material and the thickness $T_S$ of outer wall 29 may be selected to provide sufficient stiffness to enable the sheath body 14 to support the expandable balloon 50 and the catheter 30 during the introduction of the expandable balloon 50 into an introduction sheath or directly into the vasculature of a patient, such that unwanted bending and kinking of the expandable balloon 50 and the catheter 30 may be avoided. In addition, the stiffness of the sheath body 14 provided by the thickness $T_S$ of the outer wall 29 may enable the sheath body 14 to withstand, e.g., without kinking or excessive bending, the forces exerted thereupon by the expandable balloon 50 and the catheter 30 as the expandable balloon 50 is advanced through the lumen 18.

In some examples, the material and the thickness $T_S$ of the outer wall 29 may also be selected to provide adequate tearability to the sheath body 14, such that a predetermined threshold amount of force manually applied to the tabs 16A, 16B by a clinician (in a direction away from the longitudinal axis 26) causes splitting of the sheath body 14.

In some examples, the material of the outer wall 29 also may include a visible marking identifying the composition of the material or one or more dimensions of the splittable sheath. In some cases, it may be advantageous for a clinician or other user to be able to distinguish between different example splittable sheaths by identifying a material of the splittable sheath. For example, some materials of the splittable sheaths described herein may be desirable for use in procedures involving drug-coated balloons, such as the lubricious material described above. The visible marking may include a color of the material, symbols or lettering etched or printed onto an outer surface of the outer wall 29, or a visible additive material embedded within the outer wall 29.

FIGS. 5A-5C illustrate another example splittable sheath 70 that can be used with the medical device 10 of FIGS. 1-3. FIG. 5A is a perspective view of the splittable sheath 70, FIG. 5B is a side view of the splittable sheath 70, and FIG. 5C is another side view of the splittable sheath 70. The splittable sheath 70 includes a sheath body 74 having a distal end 80 and a proximal end 82, the sheath body 74 defining a lumen 78 having a greatest dimension $W_S$ (e.g., a diameter of the lumen 78, measured perpendicular to a central longitudinal axis 86 of the sheath body 74). One or more features of the splittable sheath 70 of FIGS. 5A-5D may be substantially similar to the corresponding features of the splittable sheath 12 described above with respect to FIGS. 1-4D, and will not be discussed again in detail here. For example, the splittable sheath 70 may include a first tab 90A and a second tab 90B that are substantially similar in shape and dimension to the tabs 16A, 16B described above with respect to FIGS. 1-4D. The first tab 90A includes a first major surface 92A having an outer edge 94A including a serpentine shape similar to the shape of the first outer edge 19A of the first tab 16A. Similarly, the second tab 90B shown in FIG. 5A includes a second major surface 92B having an outer edge 94B that includes a serpentine shape similar to the shape of the second outer edge 19B of the second tab 16B. The splittable sheath 70 differs from the splittable sheath 12 shown in FIGS. 1-4D in that the outer wall of the sheath body 74 is formed from multiple layers 84, 88 of material. As discussed below, the layers 84, 88 of the sheath body 74 may be formed from the same material, or may be formed from different materials that are selected to provide different functions and/or properties.

The side view of FIG. 5C shows the splittable sheath 70 rotated approximately 90° about the central longitudinal axis 86 of the sheath body 74 from the view shown in FIG. 5B. The tabs 90A, 90B can be seen in profile in FIG. 5C, with a space 96 between the tabs 90A, 90B. Due to the perspective of FIG. 5C, the serpentine shape of the outer edges 94A, 94B is not visible from this perspective, although a thickness $T_T$ of each of the tabs 90A, 90B is shown. In some examples, such as examples in which the tabs 90A, 90B are formed from the same tube as the sheath body 74, the tabs 90A, 90B each includes the inner layer 84 and the outer layer 88. Thus, the thickness $T_T$ of each of the tabs 90A, 90B may be substantially similar to a combined thickness $T_S$ of the inner layer 84 and the outer layer 88. In other examples, however, the thickness $T_T$ of each of the tabs 90A, 90B may be greater than the combined thickness $T_S$ of the inner layer 84 and the outer layer 88, or may be less than the combined thickness $T_S$. For example, the tabs 90A, 90B, as well as other tabs of splittable sheaths described herein, may be formed from different materials than the sheath body 74, or may be formed from the same materials the sheath body 74, but may also include an additional layer. The additional layer may, for example, help increase the friction of the tabs 90A, 90B, which, alone or together with the increased thickness of the tabs may help facilitate gripping of the tabs 90A, 90B by a clinician. For example, the additional layer may be a material that is more tacky or provides more friction when interfacing with surgical gloves.

FIG. 5D is a cross-sectional view of the splittable sheath 70 of the device 10 of FIGS. 1-3, the cross-section taken along line C-C in FIG. 5C, which extends orthogonal to the central longitudinal axis 86 of the sheath body 74 and in the x-y plane. The perspective provided by the cross-section of FIG. 5D faces distally toward the distal end 80 of the sheath body 74. As with the outer wall 29 of the sheath body 14 of FIGS. 1-4D, the outer layer 88 of the sheath body 74 may be a material of the amide family, such as a polyamide or a polyamide block copolymer (e.g., PEBAX or other member of the PEBA family), and may include, in some examples, a visible marking identifying the composition of the material. The material and configuration of the outer layer 88 may be chosen to provide more friction (e.g., a higher coefficient of friction) when interfaced with, for example, a surgical glove, to prevent slippage and enhance gripping.

As illustrated in FIG. 5D, the sheath body 74 of the splittable sheath 70 further includes an inner layer 84 disposed radially inward of the outer layer 88 of the sheath body 74. The inner layer 84 and the outer layer 88 may be formed by co-extrusion, or may be formed separately and then assembled by welding or other suitable techniques. In some examples, the inner layer 84 of the sheath body 74 may be made from at least a polytetrafluoroethylene (PTFE), a high-density polyethylene (HDPE), a low-density polyethylene (LDPE), or combinations thereof.

In some examples, the inner layer 84 of the sheath body 74 may have a lower coefficient of friction relative to the expandable balloon 50 of the catheter 10 than the outer layer 88. That is, the material of the inner layer 84 provides reduced resistance to the outer surface 51 of the expandable balloon 50 relative to the material of the outer layer 88.

In some cases, it may be advantageous to reduce the sliding resistance between the expandable balloon 50 and a material of an inner surface of the sheath body 74 as the expandable balloon 50 is advanced through the lumen 78 of the sheath body 74. For example, a sheath material having a relatively low coefficient of friction may help preserve the integrity of a drug coating on the outer surface 51 of the expandable balloon 50, and may reduce an amount of force needed to advance the expandable balloon 50 distally through the lumen 78 of the sheath body 74 relative to a material having a higher coefficient of friction. A threshold amount of force may be needed to overcome the friction between the expandable balloon 50 and the inner surface of the sheath body 74 in the inner lumen 78. Reducing this threshold amount of force may help provide the clinician with enhanced control over the expandable balloon 50 during introduction of the expandable balloon 50 into an introducer sheath or into the vasculature of a patient.

Materials that provide a relatively low coefficient of friction relative to the surface 51 of the expandable balloon 50 typically are relatively flexible unless configured to be relatively thick. Thus, forming the entire sheath body 74 from the low coefficient of friction layer 84 may not impart the sheath body 74 with the desired structural integrity or other properties for, e.g., protecting the expandable balloon 50 from external forces during transportation and storage of the medical device 10 without making the sheath body 74 relatively thick. Thus, in the example shown in FIGS. 5A-5C, the sheath body 74 may also include the other layer 88, which alone or together with the inner layer 84, imparts the desired structural integrity to the sheath body 74 without having to be excessively thick.

The material of the outer layer 88 may have mechanical properties (e.g., at least one of a compressive strength, a yield strength, or a tensile strength) that is stronger than the mechanical properties of the inner layer 84. Thus, increasing the relative thickness of the outer layer 88 with respect to the thickness of the inner layer 84 may provide a sheath body 74 having at least one of an increased compressive strength, a yield strength, or a tensile strength. Similarly, decreasing the relative thickness of the outer layer 88 with respect to the thickness of the inner layer 84 may provide a sheath body 74 having at least one of a decreased compressive strength, a yield strength, or a tensile strength. In some examples, the desired degree of overall stiffness or flexibility of the sheath body 74 may be based on any of several considerations, such as the dimensions of the expandable balloon 50 and the catheter 30.

As shown in FIG. 5D, the sheath body 74 may have a total thickness $T_S$. In some examples, the inner layer 84 may account for about 10% to about 30% of the total thickness $T_S$ of the sheath body 74, whereas the outer layer 88 may account for about 70% to about 90% of the total thickness $T_S$ of the sheath body. For example, the inner layer 84 may have a thickness of about 0.10 mm, and the outer layer 88 may have a thickness of about 0.30 mm. However, the relative thicknesses of the inner layer 84 and the outer layer 88 may vary in different examples, and may be based on a desired degree of stiffness or flexibility of the sheath body 74.

Forming only a part of the total thickness $T_S$ of the sheath body 74 from the higher compressive strength, yield strength, or tensile strength material may help facilitate the splitting of the sheath body 74 into two portions in response to the application of force to the tabs 92A, 92B in a direction away from the central longitudinal axis 86. Compared to a sheath body formed entirely of the higher compressive strength, yield strength, or tensile strength material of the outer layer 88, for a given sheath thickness, less force may be required to cause the splitting of the sheath body 74.

Figure 6:
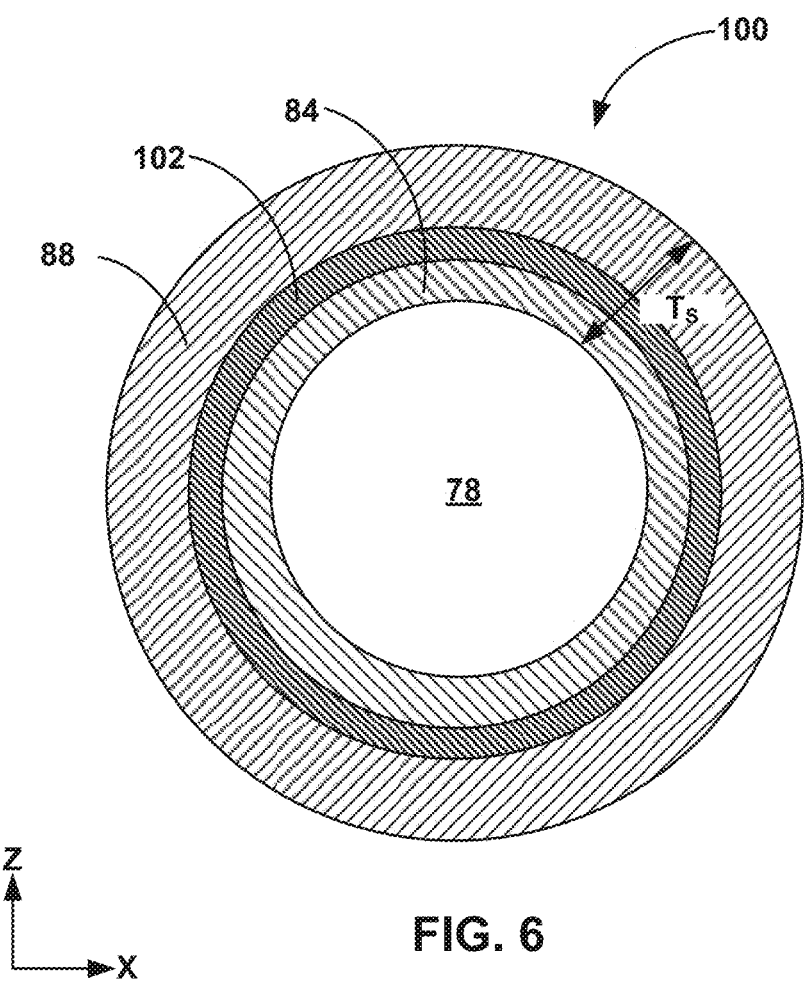
FIG. 6 is a cross-sectional view of another example splittable sheath, where a sheath body of the sheath includes an outer wall having an inner layer, an intermediate layer, and an outer layer.

In some examples, a sheath body of a sheath may include one or more additional layers in addition to or instead of the inner layer 84 and the outer layer 88. For example, as shown in FIG. 6, which is a cross-sectional view of a sheath body 100 of a splittable sheath (similar to the splittable sheaths 12 and 70 described above), the sheath body 100 may include an intermediate layer 102 between the inner and outer layers 84, 88. The cross-sectional view shown in FIG. 6 is a cross-section taken in a direction perpendicular to a longitudinal axis of the sheath body 100. The perspective provided by the cross-section of FIG. 6 faces distally toward a distal end of the sheath body 100.

In some examples, the inner and outer layers 84, 88 of the sheath body 100 may be configured such that direct adhesion to each other may be difficult to achieve, may result in a weak bond between that layers 84, 88 due to the compatibility between the layers 84, 88, or any combination thereof. Thus, in some examples, the intermediate layer 102 may help facilitate the mechanical connection of the layers 84, 88 to each other. For example, the intermediate layer 102 may be a bonding layer that is configured to bond the material of the inner layer 84 to the material of the outer layer 88. Additionally, or alternatively, the intermediate layer 102 may promote splitting of the sheath body 94 into multiple portions as a clinician moves the tabs 90A, 90B outwardly with respect to the central longitudinal axis 86 of the sheath body 100. In some examples, the inner layer 84, intermediate layer 102, and the outer layer 88 may be formed separately by any suitable techniques, and then assembled by placing the intermediate layer 102 between the inner layer 84 and the outer layer 88, and then applying sufficient heat, pressure, or other means to bond the layers together. In other examples, the inner layer 84, intermediate layer 102, and the outer layer 88 may be co-extruded together, so as to form a more integral structure.

In some examples, the intermediate layer 102 may be an adhesive material, such as, but not limited to, a thermoplastic. As shown in FIG. 6, the sheath body 100 may have a total thickness $T_S$. In some examples, the intermediate layer 102 may account for about 5% to about 15% of the total thickness $T_S$ of the sheath body 100. The inner layer 84 and the outer layer 88 may account for the remaining 85% to 95% of the thickness $T_S$. For example, the relative thicknesses of inner layer 84 and the outer layer 88 may be a ratio of about 1:3 to about 1:6. As an example, the intermediate layer 102 may account for about 10% of the thickness $T_S$, the inner layer 84 may account for about 20% of the thickness $T_S$, and the outer layer 88 may account for about 70% of the thickness $T_S$. As with the sheath body 74 of FIGS. 5A-5D, the relative thicknesses of the inner layer 84 and the outer layer 88 of the sheath body 100 may vary in different examples, and may be based on a desired degree of stiffness or flexibility of the sheath body 100.

In some examples in which the sheath body 100 includes the tabs 90A, 90B (shown in FIGS. 5A-4C), the thickness $T_T$ of each of the tabs 90A, 90B may be substantially similar to a combined thickness $T_S$ of the inner layer 84, the outer layer 88, and the intermediate layer 102. In other examples, however, the thickness $T_T$ of each of the tabs 90A, 90B may be greater than the combined thickness $T_S$ of the layers 94, 88, 102 of the sheath body 100, or may be less than the combined thickness $T_S$.

In some cases, it may be advantageous for a sheath body of a splittable sheath to be configured to preferentially split along one or more predetermined paths. For example, the preferential splitting of the sheath body may enable a clinician to better predict how the sheath body will operate during use, which may allow the clinician to better orient the sheath body relative to a catheter body or the clinician during a medical procedure. In some examples, a sheath body is configured to preferentially split along one or more grooves defined by the sheath body, the grooves defining the predetermine paths for the splitting of the sheath body into separate portions. The grooves reduce a thickness of an outer wall of a sheath body, and, as a result, for a given outer wall thickness and material, a threshold amount of force needed to split the sheath may be reduced relative to a sheath that does not include such grooves.

Figure 7B:
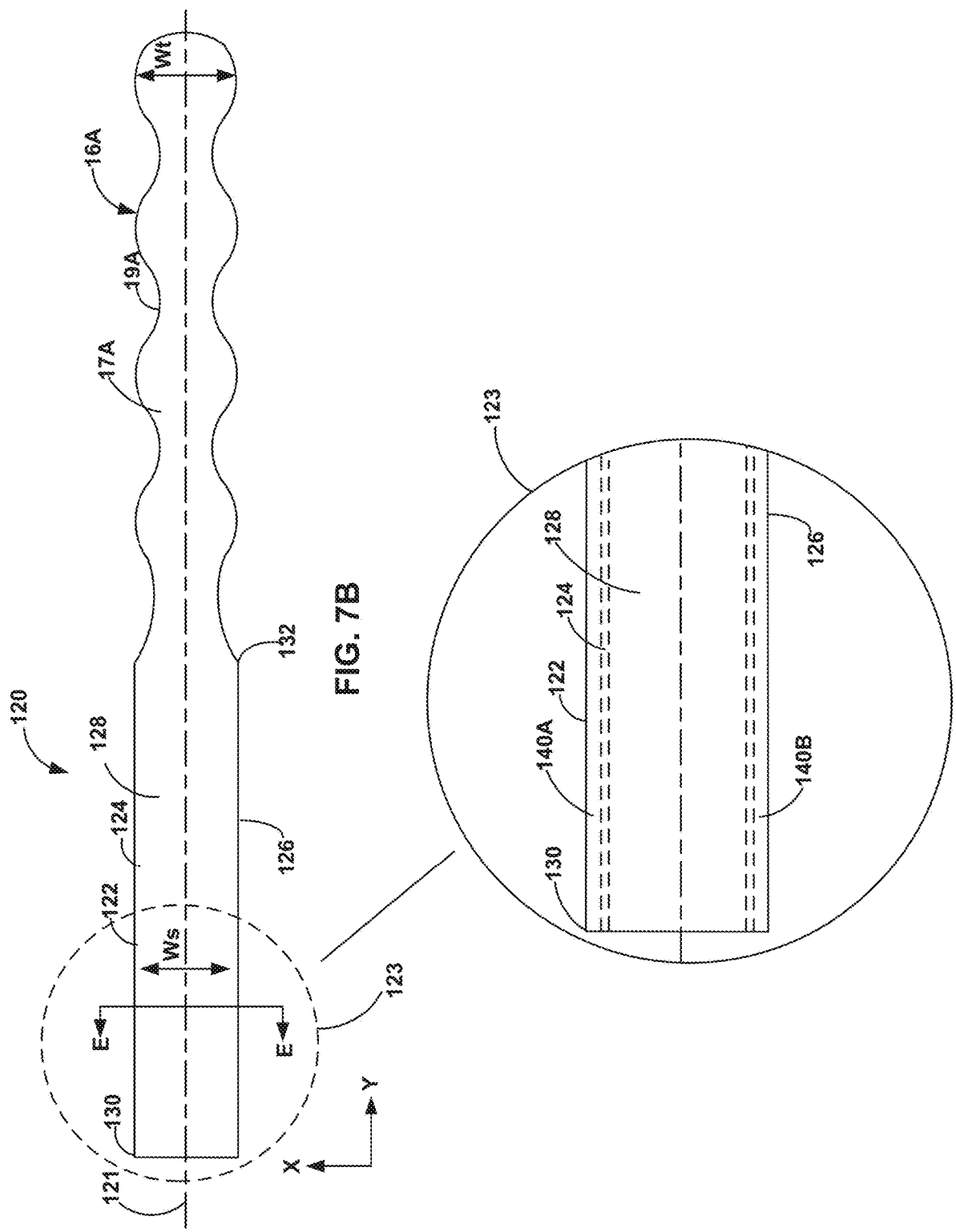
FIG. 7B is another side view of the splittable sheath of FIG. 7A.
Figure 7C:
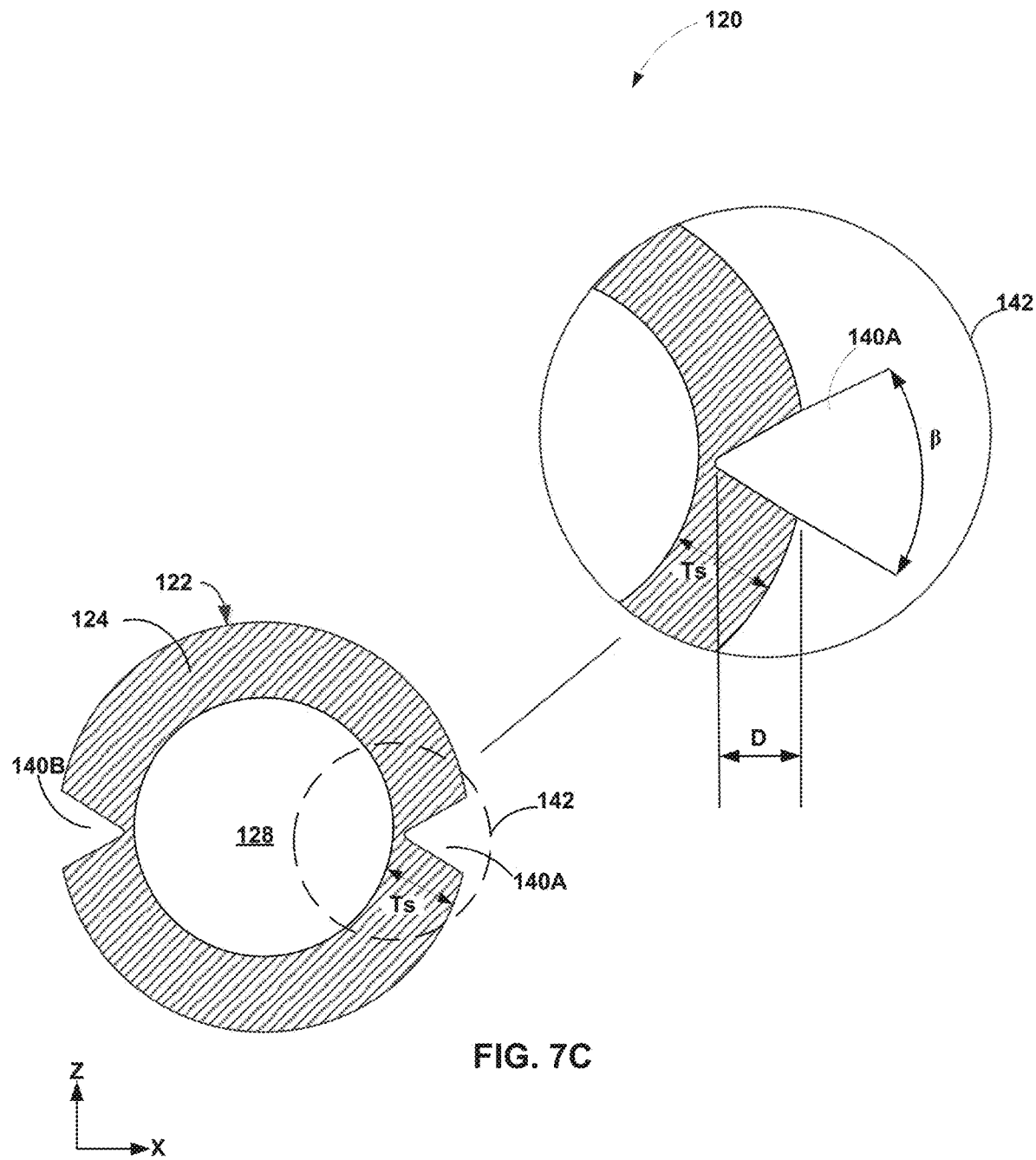
FIG. 7C is a cross-sectional view of the splittable sheath of FIG. 7A, where the cross-section is taken along a plane D-D orthogonal to a longitudinal axis of the sheath.

FIGS. 7A and 7B are side views of another example splittable sheath 120 that is configured to preferentially split along one or more predetermined paths. The splittable sheath 120 may be used with the device 10 of FIGS. 1-3. The views shown in FIGS. 7A and 7B are rotated about 90° relative to each other. The region 123 in FIG. 7B provides an enlarged view of the groove 140A. FIG. 7C is a cross-sectional view of the sheath 120, where the cross-section is taken along line D-D in FIG. 7B, in a direction perpendicular to longitudinal axis 121 of the sheath 120.

The splittable sheath 120 includes a sheath body 122 having an outer wall 124 defining an outer surface 126 of the sheath body 122. The sheath body 122 defines lumen 128 and extends from a distal end 130 to a proximal end 132. The lumen 128 having a greatest dimension $W_S$ (e.g., a diameter of the lumen 128, measured perpendicular to a central longitudinal axis 121 of the sheath body 122). One or more features of the splittable sheath 120 of FIGS. 7A and 7B may be substantially similar to the components of the splittable sheath 12 described above with respect to FIGS. 1-4D, and will not be discussed again in detail here. For example, the splittable sheath 120 may include the tabs 16A, 16B described above with respect to FIGS. 1-4D. In addition, the splittable sheath 120 may include a polyamide or a polyamide block copolymer material (e.g., PEBAX or other member of the PEBA family), and may include, in some examples, a visible marking identifying the composition of the material.

The tabs 16A, 16B of the splittable sheath 120 can be seen in profile in FIG. 7A, with a space 27 between the tabs 16A, 16B. Due to the perspective of FIG. 7A, the serpentine shape of the outer edges 19A, 19B of the tabs 16A, 16B, respectively, is not visible from this perspective, although a thickness $T_T$ of each of the tabs 16A, 16B is shown. In some examples, the thickness $T_T$ of each of the tabs 16A, 16B may be substantially similar to the thickness $T_S$ of the outer wall 29 of the sheath body 14, as described with respect to FIG. 4D.

In addition to the features of the splittable sheath 12, the outer wall 124 of the sheath body 122 may define a feature configured to facilitate splitting of the sheath 12 in a predetermined location. For example, in the example shown in FIG. 7A, the outer wall 124 defines a first groove 140A and a second groove 140B, which each define an indentation or the like extending inward (e.g., radially inward in the case of a tubular sheath body 122) from the outer surface 126 of the outer wall 124 towards the lumen 128. The grooves 140A, 140B may also be referred to as axial grooves in some examples. In addition, the grooves 140A, 140B extend longitudinally along the outer surface 126 of the sheath body 122. In some examples, the grooves 140A, 14B extend parallel to the central longitudinal axis 121 of the sheath body 122. The grooves 140A, 140B may extend from the outer surface 126 of the outer wall 124 partially through the thickness $T_S$ of the outer wall 124 of the sheath body 122.

Due to the view shown in FIG. 7A, the second groove 140B is not visible in FIG. 7A, and is on the opposite side of the sheath body 122 from the groove 140A. For example, as shown in FIG. 7C, the second groove 140B may be diametrically opposed to the groove 140B. In other examples, however, the grooves 140A, 140B may not be diametrically opposed, but, rather, may be circumferentially spaced from each other by less than 180°.

As illustrated in FIG. 7C, the grooves 140A, 140B extend partially through the thickness $T_S$ of the outer wall 124 of the sheath body 122. Grooves 140A, 140B define a weak point in the outer wall 124 of the sheath body 122, such that the splittable sheath 120 may tend to split along the grooves 140A, 140B as the clinician moves the tabs 16A, 16B in a direction away from the longitudinal axis 121. Because the grooves 140A, 140B reduce a thickness of a portion of the outer wall 124, the grooves 140A, 140B may lower a threshold amount of force needed to split the sheath 120 relative to a sheath that does not include such grooves but has the same outer wall thickness and is formed from the same material. The reduction in a threshold-splitting force provided by the grooves 140A, 140B of the sheath body 122 may provide a clinician with enhanced control over the sheath 120 as the clinician manipulates the tabs 16A, 16B to split the sheath body 122, which in turn may result in improved efficiency of the medical procedures described herein.

The grooves 140A, 140B may be formed in the outer wall 124 using any suitable technique, such as by forming during extrusion, laser etching, selective chemical dissolution, or by using a mechanical cutting technique. In the example shown in FIG. 7A, the first groove 140A continuously extends along the outer surface 126 along a length of the sheath body 122 from the distal end 130 to the proximal end 132 of the sheath body 122. However, in other examples, one or both grooves 140A, 140B may be discontinuous along a length of the sheath body 122, e.g., the groove may define perforations along the length of the sheath body 122. The length of sheath body 122 is measured in a direction parallel to the longitudinal axis 121 and in the y-axis direction. In addition to or instead of the discontinuous groove, in other examples, one or both of the grooves 140A, 140B may extend along the outer surface 126 of the sheath body 122 from the proximal end 132 to a location proximal to the distal end 130, or vice versa. For example, the groove may extend along 50% to about 95% of the length of the sheath body 122, such as about 70% to about 80%, or about 75% of the length of the sheath body 122.

In some of examples, the grooves 140A, 140B may be positioned on substantially opposite sides of the longitudinal axis 121 of the sheath body 122, and may be substantially aligned with the major surface 17A, 17B of one or both of the tabs 16A, 16B along an axis parallel to the central longitudinal axis 121 of the sheath body 122, or aligned with any part of the tabs 16A, 16B along the same axis. This alignment between the tabs 16A, 16B and the grooves 140A, 140B may help a clinician initiate the splitting of the sheath body 122 along the grooves 140A, 140B when the clinician pulls the tabs 16A, 16B in a direction away from the longitudinal axis 121.

Although the sheath body 122 and the sheath body 154 discussed below with respect to FIGS. 8A-8C are described as having two grooves, other example sheath bodies may include only one groove or more than two grooves.

In the example shown in FIG. 7C, the grooves 140A, 140B each may have a "v" shape or another tapering shape in cross-section, with the apex of the groove positioned closer to the lumen 128 of the sheath body 122 than the wider portion of the groove. In other examples, the grooves 140A, 140B each may have other cross-sectional shapes, such as a "u" shape, a "c" shape, or any other suitable shape. The region 142 in FIG. 7C provides an enlarged view of the groove 140A, illustrating the depth "D" of the groove 140A within the outer wall 124 of the sheath body, and an angle beta ("β") that depicts the angle of the groove 140A. Although the depth and angle of the groove 140A are described with respect to the region 142, it should be noted that the groove 140B may have substantially similar characteristics.

In some examples, the depth D of the groove 140A may be approximately 70% of the thickness $T_S$ of the sheath body 122. In other examples, the depth D of the groove 140A may extend through a greater or lesser portion of the thickness $T_S$ of the outer wall 124, such as from approximately 50% to approximately 90% of the thickness $T_S$. As with other components of the example splittable sheaths described herein, the depth D of the groove 140A may be selected based on a desired degree of strength or ease of splittability of the sheath 120. For example, in examples in which relatively greater strength of the sheath 120 is desired over relatively easier splittability of the sheath 120, the depth D of the groove 140A may extend through less of the thickness $T_S$ of the outer wall 126 than when relatively easier splittability is desired. Easier splittability may be defined by, for example, a threshold amount of force needed to pull the tabs 19A, 19B apart and away from the central longitudinal axis 121 in order to split the sheath body 122.

In some examples, the angle β formed by the walls defining the groove 140A at the outer surface 126 of the sheath body 122 may extend along approximately 10° of a perimeter of the cross-section of the sheath body 122 illustrated in FIG. 7C, although the groove 140A may extend along the perimeter of cross-section of the sheath body 122 to a greater or lesser extent in other examples. In some examples, the angle β may translate to a percentage of the outer perimeter of the cross-section of the sheath body 122, such as approximately 2% to approximately 20% of such the outer perimeter. As with the depth D of the groove 140A, the angle β also may be selected based on a desired degree of strength or ease of splittability of the sheath 120. For example, in examples in which relatively greater strength of the sheath 120 is desired over relatively easier splittability of the sheath 120, the angle β of the groove 140A may be smaller than when relatively easier splittability is desired.

Figure 8:
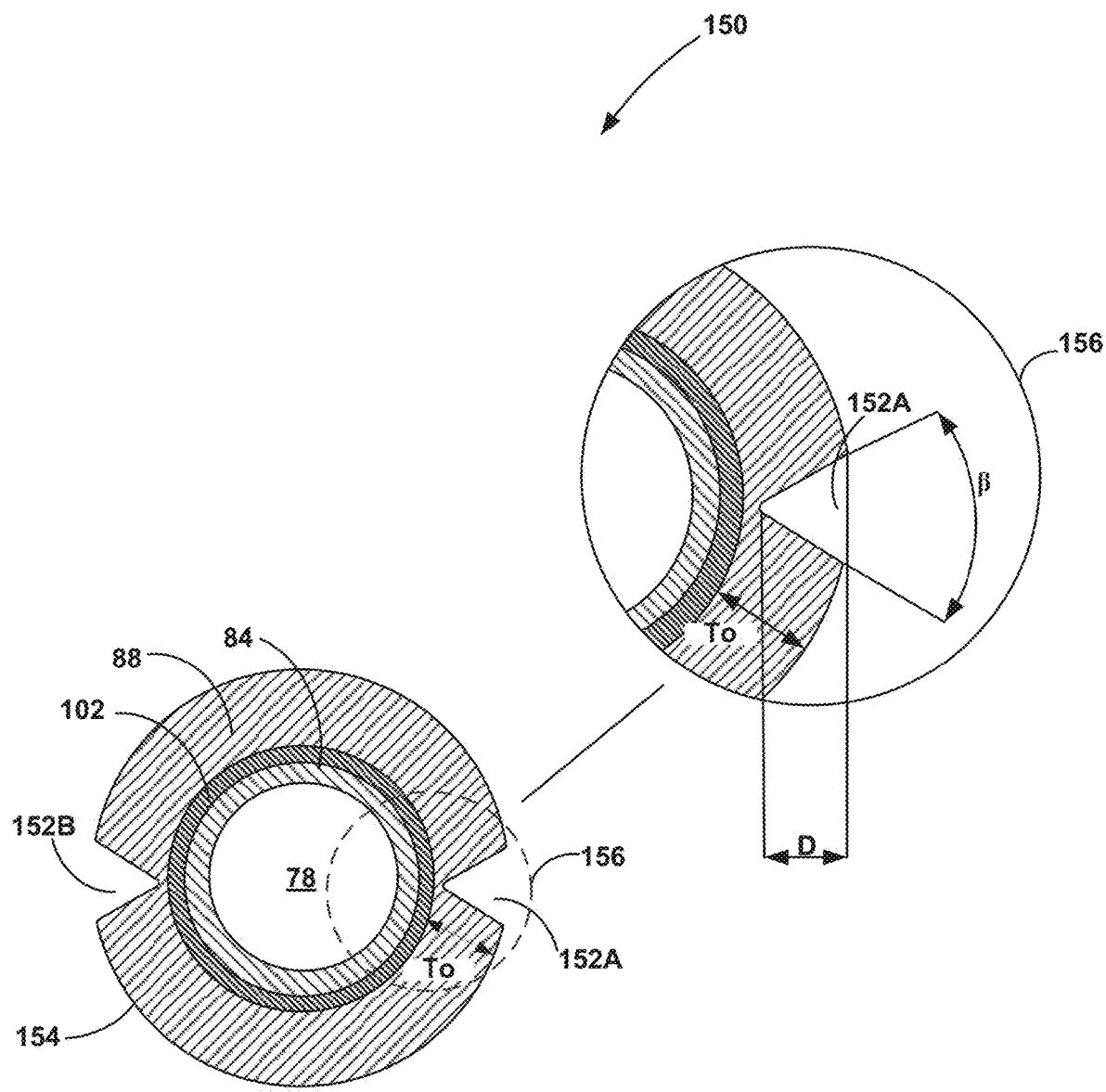
FIG. 8 is a cross-sectional view of another example splittable sheath, which includes an outer wall having an inner layer, an intermediate layer, and an outer layer, where a body of the sheath includes a first groove and a second groove extending longitudinally along an outer surface of a body of the sheath.

The cross-section of sheath 120 shown in FIG. 7C illustrates a sheath body having a single layer of material. In examples in which sheath 120 is formed from multiple layers of material, e.g., as described with respect to sheath body 74 shown in FIGS. 5A-5D, and sheath body 100 shown in FIG. 6, the grooves 140A, 140B may extend through (completely through or only partially through) only one of the layers of the sheath body, or through (completely through or only partially through) multiple layers of the sheath body (e.g., two or more layers, and, in some examples, all of the layers). An example of such a sheath body defining a groove defined by a sheath body including multiple layers is shown in FIG. 8, which is a cross-sectional view of a sheath body 150 of a splittable sheath. As with sheath body 100 (FIG. 6), the sheath body 150 may include an inner layer 84, an outer layer 88, and an intermediate layer 102 disposed between the inner and outer layers 84, 88.

The sheath body 150 defines a first groove 152A and a second groove 152B, which may be similar to the grooves 140A, 140B of the splittable sheath 120 (FIGS. 7A-7C). As illustrated in FIG. 8, the grooves 152A, 152B from an outer surface 154 of the sheath body 150 extend partially through the outer layer 88 of the sheath body 154, such that the grooves 152A, 152B are defined by only the outer layer 88 and not the inner layer 84 or the intermediate layer 102. However, in other examples, the grooves 152A, 152B may extend into the intermediate layer 102 or the inner layer 84, as an intentional design feature or as a result of some manufacturing tolerance specifications. The region 156 in FIG. 8 provides an enlarged view of the groove 152A, illustrating the depth D of the groove 152A within the outer layer 88 of the sheath body 150, and an angle beta β that depicts the angle of the groove 152A. Although the depth and angle of the groove 152A are described with respect to the region 156, it should be noted that the groove 152B may have substantially similar characteristics.

In some examples, the depth D of the groove 152A may be about 50% to about 90% of the thickness $T_O$ of the outer layer 88, such as about 55% to about 80%, or about 70% of the thickness $T_O$. In other examples, the depth D of the groove 152A may extend through an entirety of the outer layer 88 and partially or fully through into the intermediate layer 102. In addition, in other examples, the depth D of the groove 152A may extend through an entirety of the outer layer 88 and the intermediate layer 102, and partially through the inner layer 84. As with the grooves 140A, 140B of FIGS. 7A-7C, the depth D of the groove 152A may be selected based on a desired degree of strength or ease of splittability of the sheath body 150.

In some examples, the angle "β" formed by the groove 152A at the outer surface 154 of the sheath body 150 may extend along a portion of a perimeter of the cross-section of the sheath body 150, as described above with respect to the splittable sheath 120 of FIGS. 7A-7C. As with the angle β formed by the groove 140A, the angle β of the groove 152A of the sheath body 150 similarly may be selected based on a desired degree of strength or degree of splittability of the sheath body 150. However, the splittability of the sheath body 150 also may be influenced by the configuration of the intermediate layer 102 (e.g., the thickness, the material, and the like), which may increase the splittability of the sheath body 150 relative to the sheath 120 of FIGS. 7A-7C.

As discussed above, a serpentine shape of a tab of a splittable sheath can have any suitable outer perimeter, and is not limited to the shape of the outer edge 19A, 19B shown in FIGS. 4A and 4B. FIGS. 9-12 are side views of example splittable sheaths that include tabs having major surfaces that include outer edges having various serpentine shapes. For ease of description, the example splittable sheaths of FIGS. 9-12 are illustrated as including the sheath body 14 of the example of FIGS. 1-4D. However, in other examples, each of the example splittable sheaths of FIGS. 9-12 may include any of the sheath bodies 14, 74, 100, 122, and 150 of FIGS. 1-8C.

Figure 9:
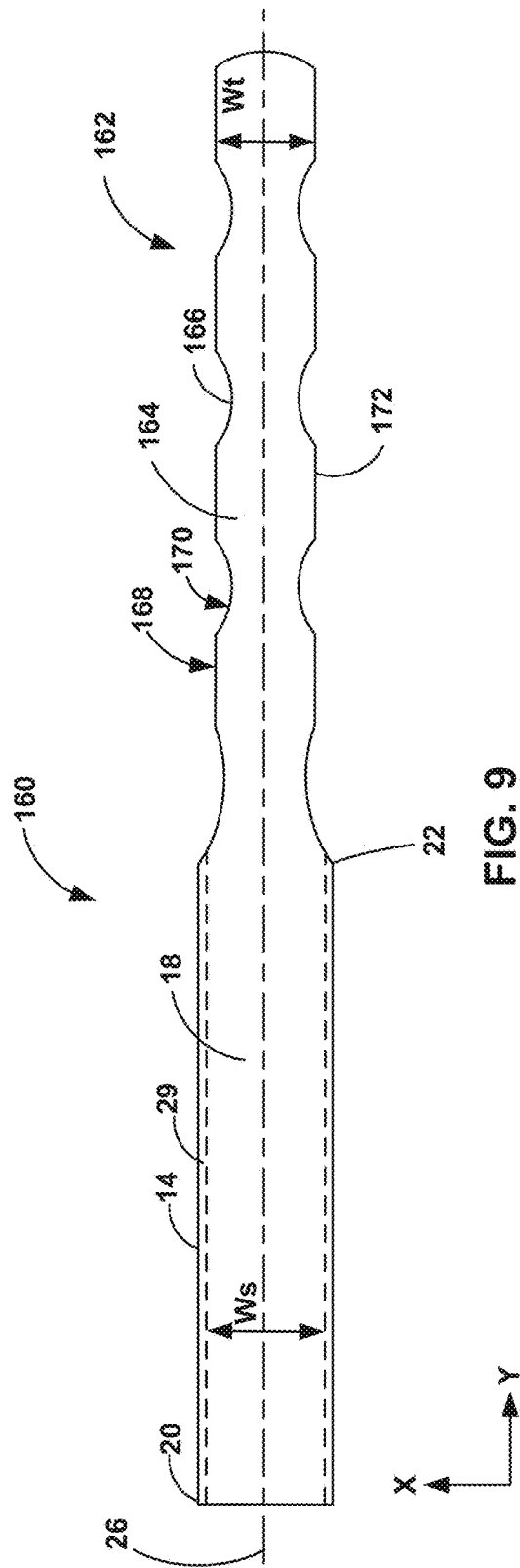
FIG. 9 is a side view of another example splittable sheath including a first tab and a second tab, and illustrates another example serpentine shape for an outer edge of a major surface of the first tab and an outer edge of a major surface of the second tab.

FIG. 9 illustrates an example splittable sheath 160 that includes a tab 162 extending proximally from the proximal end 22 of the sheath body 14. Although not shown in the side view of FIG. 9, in some examples, the splittable sheath 160 may also include a second tab extending proximally from the proximal end 22 of the sheath body 14, e.g., on the other side of central longitudinal axis 26 from tab 162. In these examples, the second tab may have a configuration similar to the tab 162. As with the splittable sheath 12 of FIGS. 1-4D, the tab 162 may extend distally from the distal end 20 of the sheath body 14 in other examples of the splittable sheath 160.

The tab 162 includes a major surface 164 defining an outer edge 166. As shown in FIG. 9, the serpentine shape of the outer edge 166 extends around an outer perimeter of the tab 162. In other examples, however, the serpentine shape may only extend around part of the tab 162, such as along only one side of the longitudinal axis 26 of the sheath body 14. The tab 162 may be similar to the first tab 16A shown in FIGS. 1-4, except that it defines a different serpentine shape In the example of FIG. 9, the outer edge 166 of the major surface 164 includes alternating outwardly-projecting portions 168 and inwardly projecting portions 170. Each outwardly-projecting portion 168 extends outwardly in the x-axis direction from the central longitudinal axis 26 of the sheath body 14 compared to the inwardly projecting portions 170. In this way, the outer edge 166 may define an undulating shape. However, in contrast to the curvilinear undulating shape of tabs 16A, 16B, the tab 162 includes the outwardly-projecting portions 168 define straight edges 172. The inwardly-curving portions 170 shown in FIG. 9 may each have any suitable shape, such as a half-circle shape or another arc, or other curved shape. Although the outer edge 166 illustrated in FIG. 9 includes four outwardly-projecting portions 168 and four inwardly-projecting portions 140, in other examples, the outer 166 may include a fewer or a greater lesser number of the outwardly-projecting portions 168 and the inwardly-projection portions 170 in other examples.

The serpentine shape of the outer edge 166 provides advantages such as gripping surfaces that helps prevent a clinician's fingers or tools from slipping while the clinician grasps the tab 162 and splits the sheath body 14. Other advantages of the serpentine shape of the outer edge 166 may be substantially similar to those described above with respect to the example serpentine shape of the outer edges of the tabs of other example splittable sheaths described herein, such as the outer edges 19A, 19B of the tabs 16A, 16B. For example, the serpentine shape of the outer edge 166 may help contribute to the ease of cleaning the of the outer edge 166 and the major surface 164 during or after the manufacturing process. In addition, the features and potential advantages described above with respect to the tab 162 of FIG. 9 are not limited to the splittable sheath of FIG. 9, but may also be applied to the tabs of the example splittable sheaths described below with respect to FIGS. 10-12.

In some examples, a greatest width $W_T$ (measured perpendicular to the central longitudinal axis 26 of the sheath body 14) of the tab 162 may less than or equal to the greatest dimension $W_S$ of the lumen 18 of the sheath body 14. In other examples, the greatest width $W_T$ of the tab 162 may be greater than the greatest dimension $W_S$ of the lumen 18 of the sheath body 14, such as examples in which the tab 162 is formed separately from the sheath body 14, or examples in which a blank tube from which the splittable sheath 160 is manufactured is wider at one end.

Figure 10:
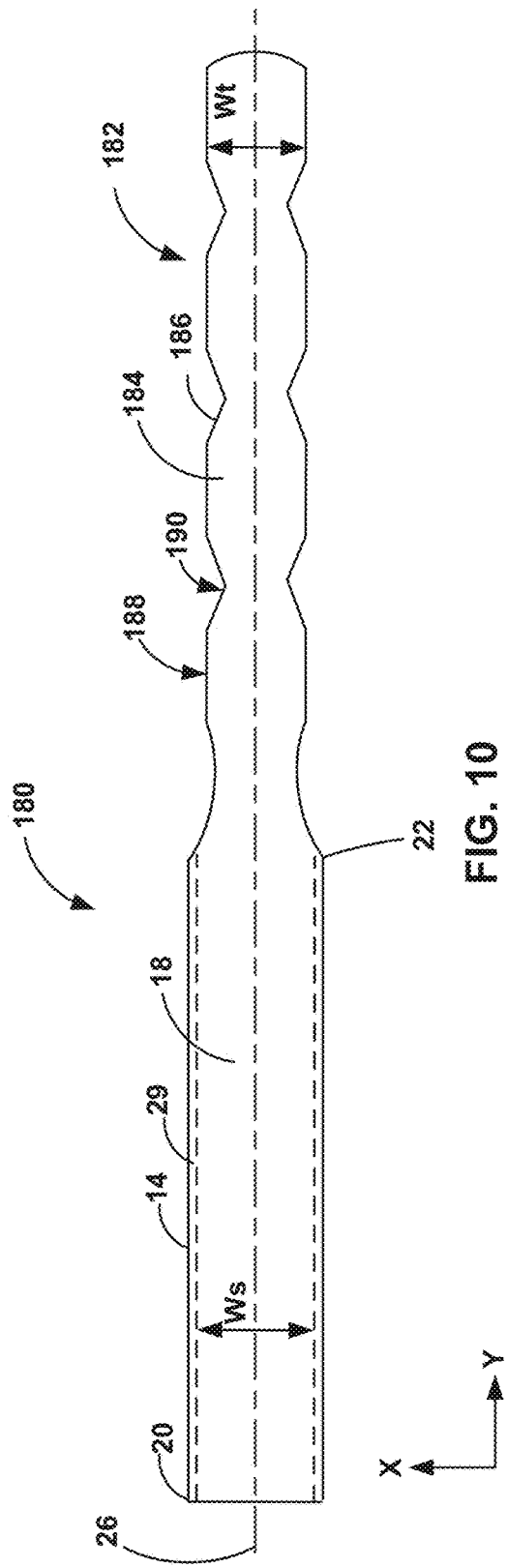
FIG. 10 is a side view of another example splittable sheath including a first tab and a second tab, and illustrates another example serpentine shape for an outer edge of a major surface of the first tab and an outer edge of a major surface of the second tab.

FIG. 10 illustrates an example splittable sheath 180 that includes a tab 182 extending proximally from the proximal end 22 of the sheath body 14. Although not shown in the side view of FIG. 10, in some examples, the splittable sheath 180 may also include a second tab extending proximally from the proximal end 22 of the sheath body 14, e.g., on the other side of central longitudinal axis 26 from tab 162. In these examples, the second tab may have a configuration similar to the tab 182. As with the splittable sheath 12 of FIGS. 1-4D, the tab 182 may extend distally from the distal end 20 of the sheath body 14 in other examples of the splittable sheath 160.

The tab 182 includes a major surface 184 defining an outer edge 186. As shown in FIG. 10, the serpentine shape of the outer edge 186 extends around an outer perimeter of the tab 182. In other examples, however, the serpentine shape may only extend around part of the tab 182, such as along only one side of the longitudinal axis 26 of the sheath body 14. The tab 182 may be similar to the first tab 16A shown in FIGS. 1-4, except that it defines a different serpentine shape In the example of FIG. 10, the outer edge 166 of the major surface 164 includes alternating outwardly-projecting portions 188 and inwardly-projecting portions 190. The outwardly-projecting portions 188 may be similar to outwardly-projecting portions 168 discussed above with respect to FIG. 9. The inwardly-projecting portions 190 each define a "v" shape or other angular shape having substantially straight edges. Tab 182 may have any suitable numbering of outwardly-projecting portions 188 and inwardly-projecting portions 190.

FIG. 11 illustrates an example splittable sheath 200 that includes a tab 202 extending proximally from the proximal end 22 of the sheath body 14. Although not shown in FIG. 11, in some examples, the splittable sheath 200 may also include a second tab on an opposite side of the longitudinal axis 26 from the tab 202. The tab 202 includes a first major surface 204 defining an outer edge 206. As shown in FIG. 11, the serpentine shape of the outer edge 206 extends around an outer perimeter of the tab 202. In other examples, however, the serpentine shape may only extend around part of the tab 202, such as along only one side of the longitudinal axis 26 of the sheath body 14. The tab 202 may be similar to the first tab 16A shown in FIGS. 1-4, except that it defines a different serpentine shape In the example splittable sheath 200 of FIG. 11, the outer edge 206 of the major surface 204 of the tab 202 defines a zig-zagging edge. Although the zig-zagging edge 206 is shown in FIG. 11 as defining v-shapes, e.g., a saw-toothed pattern, in other examples, the zig-zagging edge 206 may define another shape or a combination of shapes, such as a toothed shape. In any such examples, a greatest width $W_T$ of the tab 202 may be less than, equal to, or greater than the greatest dimension $W_S$ of the lumen 18 of the sheath body 14, as noted above.

FIG. 12 illustrates an example splittable sheath 210 that includes a tab 212. Although not shown in FIG. 12, in some examples, the splittable sheath 210 may also include a second tab on an opposite side of the longitudinal axis 26 from the tab 212. The tab 212 includes a first major surface 214 defining an outer edge 216. As shown in FIG. 12, the serpentine shape of the outer edge 216 extends around an outer perimeter of the tab 212. In other examples, however, the serpentine shape may only extend around part of the tab 212, such as along only one side of the longitudinal axis 26 of the sheath body 14. The tab 212 may be similar to the first tab 16A shown in FIGS. 1-4, except that it defines a different serpentine shape.

In the example of FIG. 12, the outer edge 216 of the major surface 214 includes alternating outwardly-projecting portions 218 and inwardly-projecting portions 220. Each of the portions 218, 220 have an angular "u" shape, a modified angular "u" shape, or other angular shape. In some examples, a shape of the outwardly-projecting portions 218 may be similar to an inverted shape of the inwardly-projecting portions 220, as shown in FIG. 12. In any such examples, a greatest width $W_T$ of the tab 212 may be less than, equal to, or greater than the greatest dimension $W_S$ of the lumen 18 of the sheath body 14, as noted above.

The various example shapes of the outer edges of the tabs of the example splittable sheaths described herein is intended to be illustrative and not exhaustive. In some examples, variations on the example shapes of the outer edges illustrated in FIGS. 9-12 may be modified, such as by varying the spacing between any of the outwardly-projecting portions, by combining two or more of the shapes illustrated herein, by modifying a dimension of any portion of a shape of an outer edge relative to another portion of the shape of the outer edge, using a different serpentine shape (e.g., undulating or toothed shape), and the like. In some examples, a shape of the outer edges of the one or more tabs of a splittable sheath may be selected based on relative gripability of a particular shape, ease of cleaning of a particular shape, or cost of manufacturing a particular shape, although other considerations also may affect a choice of the shape of the outer edges of the tabs. In all examples described herein, the shapes of the outer edges of the tabs may provide one or both of enhanced gripability and ability to be sterilized relative to example sheaths that lack gripping features or that rely on tabs having texturized major surfaces to enhance gripability.

Figure 13:
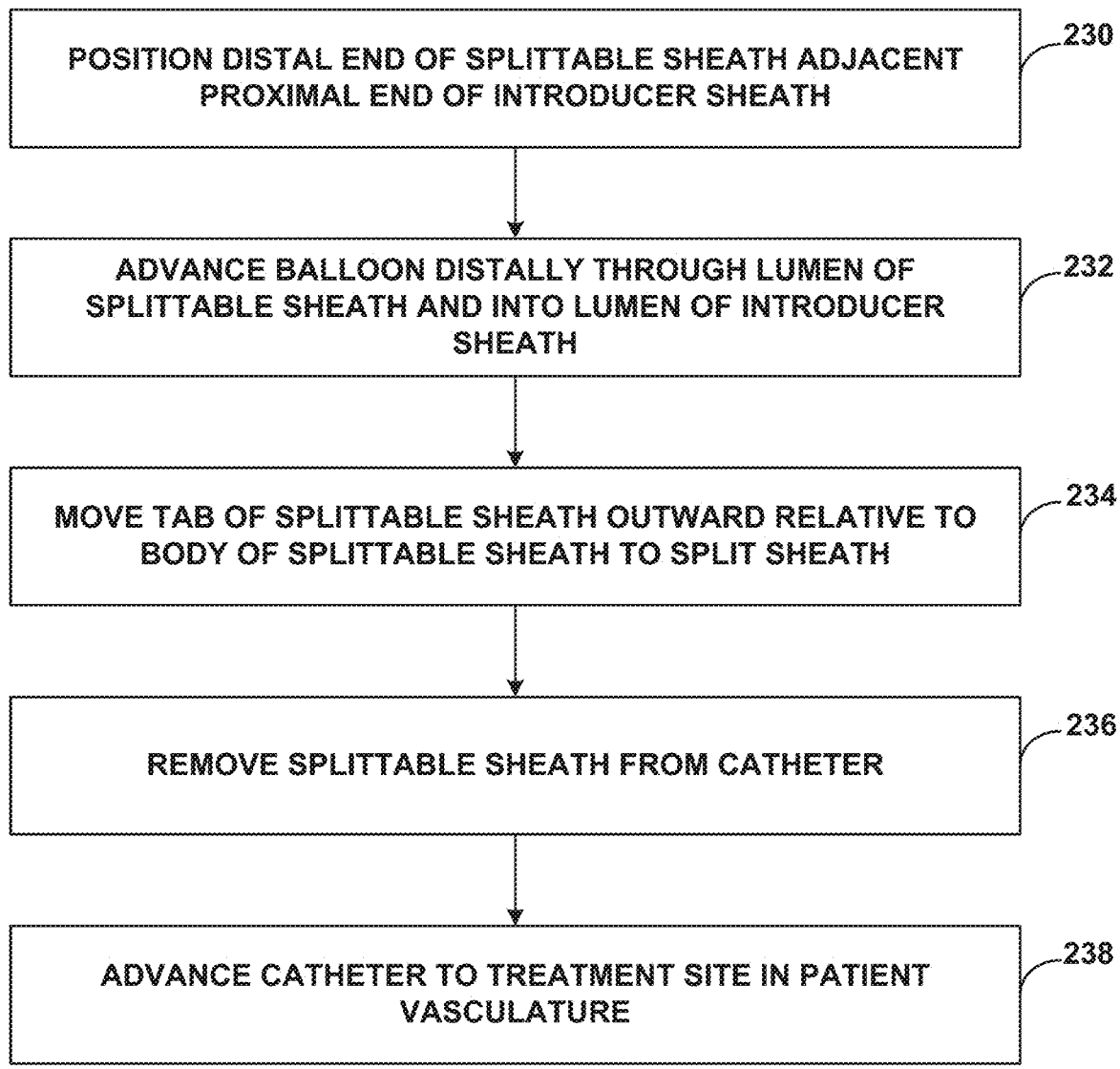
FIG. 13 is a flow diagram illustrating an example method of using a medical device as described herein.

FIG. 13 is a flow diagram illustrating an example technique that may be implemented by a clinician to deploy and use a medical device, such as the medical device 10, within the vasculature of a patient as described herein. The flow diagram of FIG. 13 is described in conjunction with FIGS. 14A-14E, which illustrate a series of side views showing the expandable balloon 50 of the medical device 10 of FIG. 1 being advanced through the splittable sheath 12 and into a vessel 240 of a patient 242, as well as the splitting and removal of the splittable sheath 12 from the catheter 30. While FIG. 13 is described in context with the splittable sheath 12 of FIGS. 1-4D, the techniques of FIG. 13 may be used in conjunction with other techniques or other splittable sheaths (e.g., the splittable sheaths of FIGS. 5A-12). In addition, in the example of FIGS. 14A-14E, an introducer sheath 244 is illustrated as being inserted through the skin 246 of the patient 242 and into the vessel 240. In some examples, the introducer sheath 244 may be inserted through skin 246 of the patient 242 prior to a step of positioning the distal end 20 of the sheath body 14 adjacent the proximal end 244A of the introducer sheath 244. In other examples, an introducer sheath may not be used in the technique illustrated in FIGS. 14A-14E, or an introducer sheath having a different configuration than the introducer sheath 244 may be substituted.

Figure 14A:
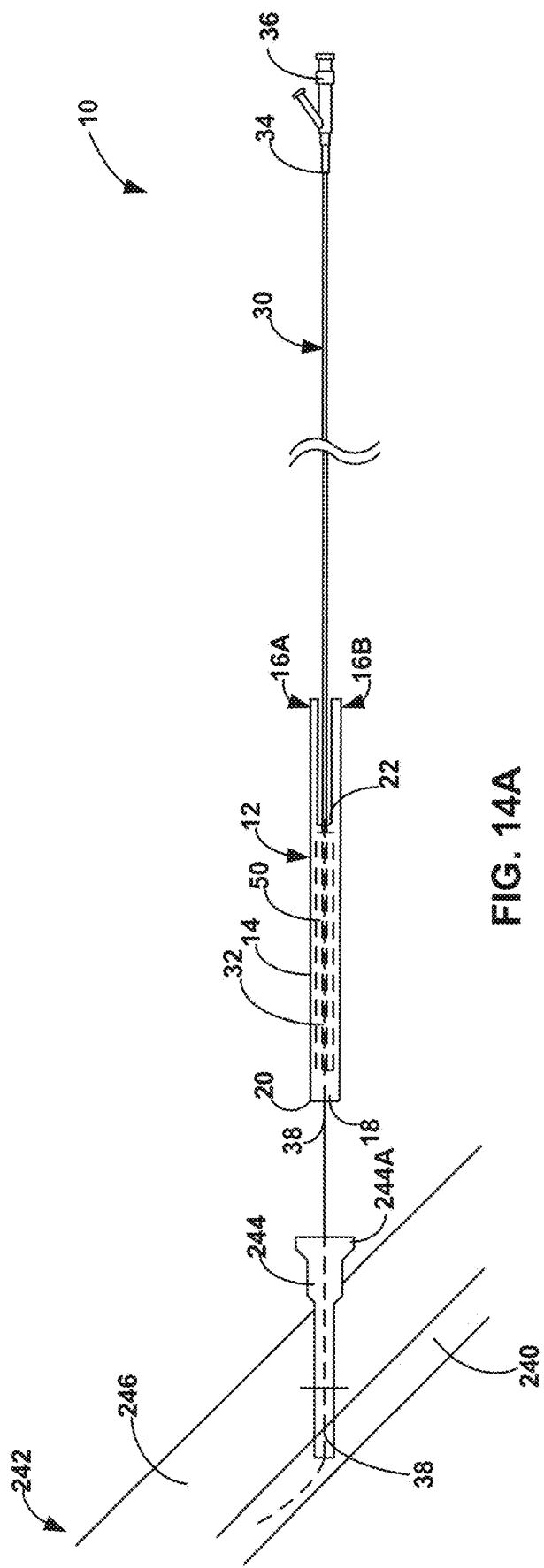
FIGS. 14A-14E are a series of side views showing an example medical device being operated in accordance with the techniques described with respect to the example method of FIG. 13.

As shown in FIG. 14A, the distal end 20 of the sheath body 14 may be advanced over the guidewire 38, which may extend distally from the distal end 20 of the sheath body 14, through the introducer sheath 244, and into the vessel 240. In the illustrated example, the guidewire 38 also extends proximally from the distal end 20 of the sheath body 14, into the lumen 18, and through the catheter 30 on which the expandable balloon 50 is positioned. The guidewire 38 may extend further proximally through a portion of the catheter 30 that extends proximally of the tabs 16A, 16B of the splittable sheath 12 and into the hub 36, from which a clinician may manipulate the guidewire 38 as needed.

Figure 14B:
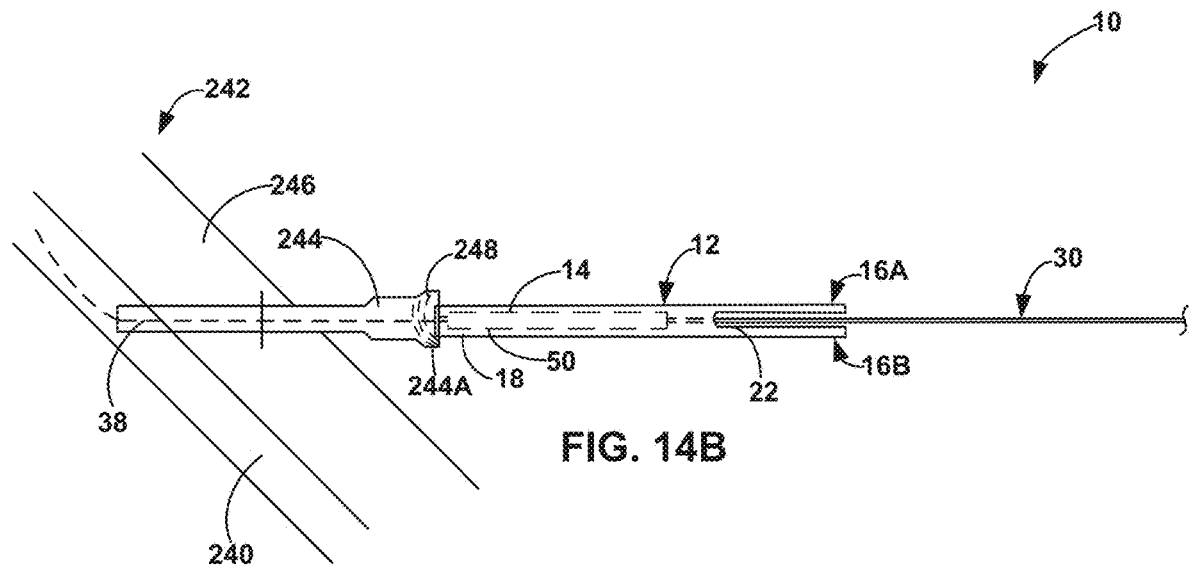

The technique of FIG. 13 includes positioning the distal end 20 of the sheath body 14 of the splittable sheath 12 adjacent a proximal end 244A of the introducer sheath 244 (230), as shown in FIG. 14B. In some examples, the distal end 20 of the sheath body 14 may be configured to be securely received within the proximal end 244A of the introducer sheath 244, such as by a mating connection therebetween. In some such examples, the distal end 20 of the sheath body 14 may be stably received by the introducer sheath 244 to enable a smooth transfer of the expandable balloon 50 from the lumen 18 of the sheath body 14 to the introducer sheath 244. For example, the distal end 20 of the sheath body 14 may function as a male Luer adapter that engages a feature of the introducer sheath 244 that may function as a female Luer adapter, and one or more threads or projections 248 positioned on an internal surface of the introducer sheath 244. The threads or projections 248 of the introducer sheath 244 may be configured to mechanically engage with the distal end 20 of the sheath body 14 and separably retain the distal end 20 of the sheath body within the introducer sheath 244. In other examples, the distal end 20 of the sheath body 14 may engage the introducer sheath 244 by merely being received in a recess defined by the introducer sheath 244, without any threaded engagement therebetween.

Figure 14C:
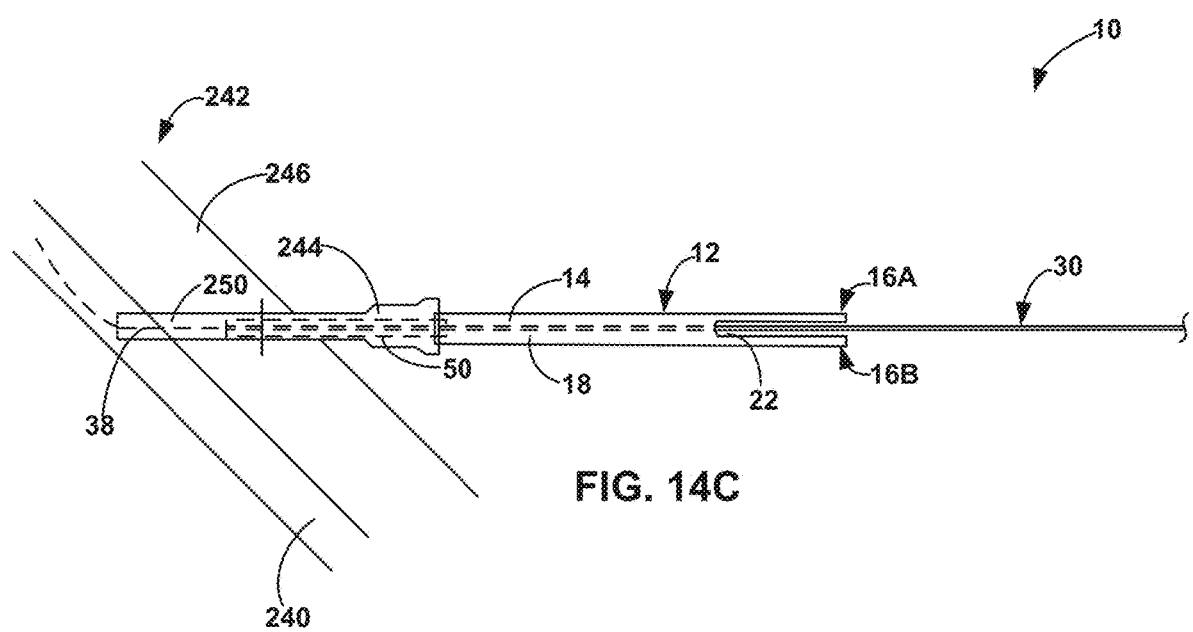

As illustrated in FIG. 14C, the clinician advances the expandable balloon 50 distally through the lumen 18 of the sheath body 14 and into a lumen 250 of the introducer sheath 244 (232). In some examples, the clinician may advance the expandable balloon 50 distally into the lumen 250 of the introducer sheath 244 by applying a distally-directed force to a portion of the catheter 30 that extends proximally of the splittable sheath 12 or to the hub 36 (shown in FIG. 1). In some such examples, the clinician may advance the expandable balloon 50 and catheter 30 over the guidewire 38 into the introducer sheath 244 while the splittable sheath 12 remains substantially stationary relative to the introducer sheath 244 while the catheter 30 and the expandable balloon 50 move relative to the splittable sheath 12, as depicted by the relative positioning of the splittable sheath 12 and the expandable balloon 50 in FIG. 14B and FIG. 14C. Thus, the clinician may advance the expandable balloon 50 through the lumen 18 of the splittable sheath 12, through the lumen 250 of the introducer sheath 244 and into the vessel 240 of the patient 242 without manually handling the balloon 50 or otherwise exposing the external surface 51 of the expandable balloon 50 to the exterior of the splittable sheath 12 while the expandable balloon 50 is being inserted. As discussed above, minimizing directly physical contact with the expandable balloon 50 may help avoid loss of drug coating, kinking, stretching, or self-adhesion of balloon components that may occur during handling if the expandable balloon 50 is not protected.

Figure 14D:
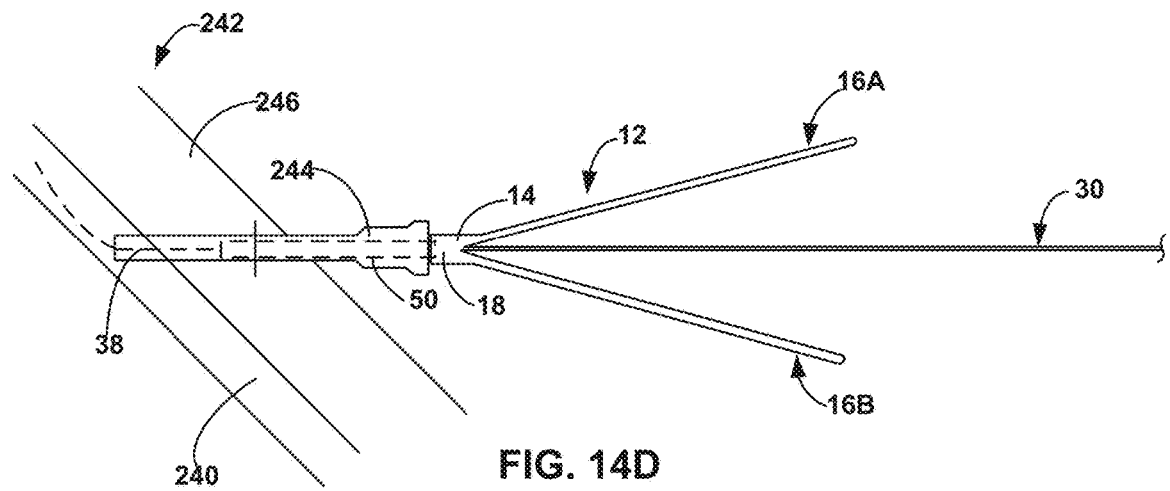

Once the expandable balloon 50 has been advanced through the lumen 18 of the sheath body 14 and into the introducer sheath 244, the clinician may grasp the tabs 16A, 16B and move the tabs 16A, 16B outwardly relative to the central longitudinal axis 26 (shown in FIG. 4A) of the sheath body 14 to split the sheath body 14 into multiple portions (234). As shown in FIG. 14D, the sheath body 14 may split in a proximal-to-distal direction as the tabs 16A, 16B are moved outward. In examples in which the tabs 16A, 16B extend from the distal end 20 of the sheath body 14, outward movement of the tabs 16A, 16B relative to the central longitudinal axis 14 may cause the sheath body to split in a distal-to-proximal direction.

The serpentine shape of the outer edges 19A, 19B (shown in FIG. 4A) of the tabs 16A, 16B provides a gripping surface for the clinician's fingers as the clinician grasps the tabs 16A, 16B to split the splittable sheath 12 once the expandable balloon has been advanced through the lumen 18 and into the introducer sheath 244. As discussed above, the shape of the outer edges 19A, 19B helps secure the clinician's grip on the tabs 16A, 16B while splitting the splittable sheath 12, such that sudden splitting of the sheath body 14 and an unintended transfer of force to other portions of a medical device, which may dislodge the introducer sheath 244 or the guidewire 38 from the vessel 240, may be avoided. The shape of the outer edges 19A, 19B thus may help increase the efficiency of the technique of FIG. 13.

Figure 14E:
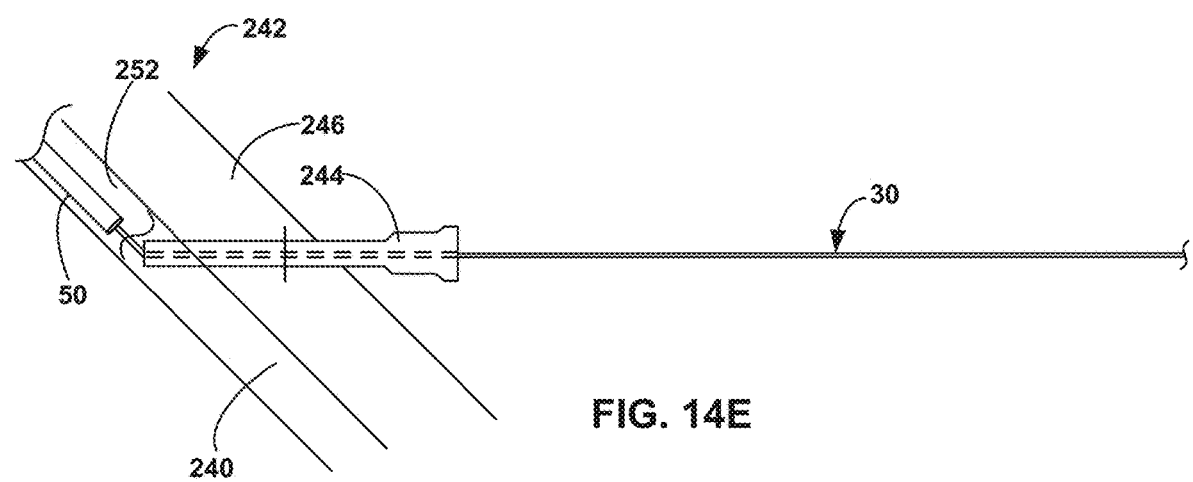

The clinician may continue to move the tabs 16A, 16B outward (away from the longitudinal axis of the sheath body 14) from the configuration illustrated in FIG. 14D to fully split the sheath body 14 into two separate portions. With the sheath body 14 in two separate portions, the sheath body 14 then may be removed from over the catheter 30 (236). In other examples, the two portions of the sheath body 14 may not be entirely separated but may remain attached by a portion of the sheath body 14. With the splittable sheath 12 removed from the catheter 30, the clinician then may advance the expandable balloon 50 through the vessel 240 to the treatment site 252, as shown in FIG. 14E (238). In some examples, the treatment site 252 may be located in a portion of the vessel 240. In other examples, the treatment site 252 may be located within a vessel that branches off from the vessel 240.

Removing the splittable sheath 12 from the catheter 30 enables the clinician to advance substantially all of the usable length of the catheter 30 into the vasculature of the patient 242 if needed, thereby enabling the expandable balloon 50 to be delivered to more distal treatment sites than example medical devices in which a balloon sheath is not removable from a catheter on which a balloon or other intravascular medical devices is positioned. Once the expandable balloon 50 is positioned at the treatment site 252, the clinician then may introduce a fluid into the expandable balloon 50 to inflate the same and continue performing the medical procedure, which may include placing a stent or delivering drug at the treatment site 252.

Figure 15:
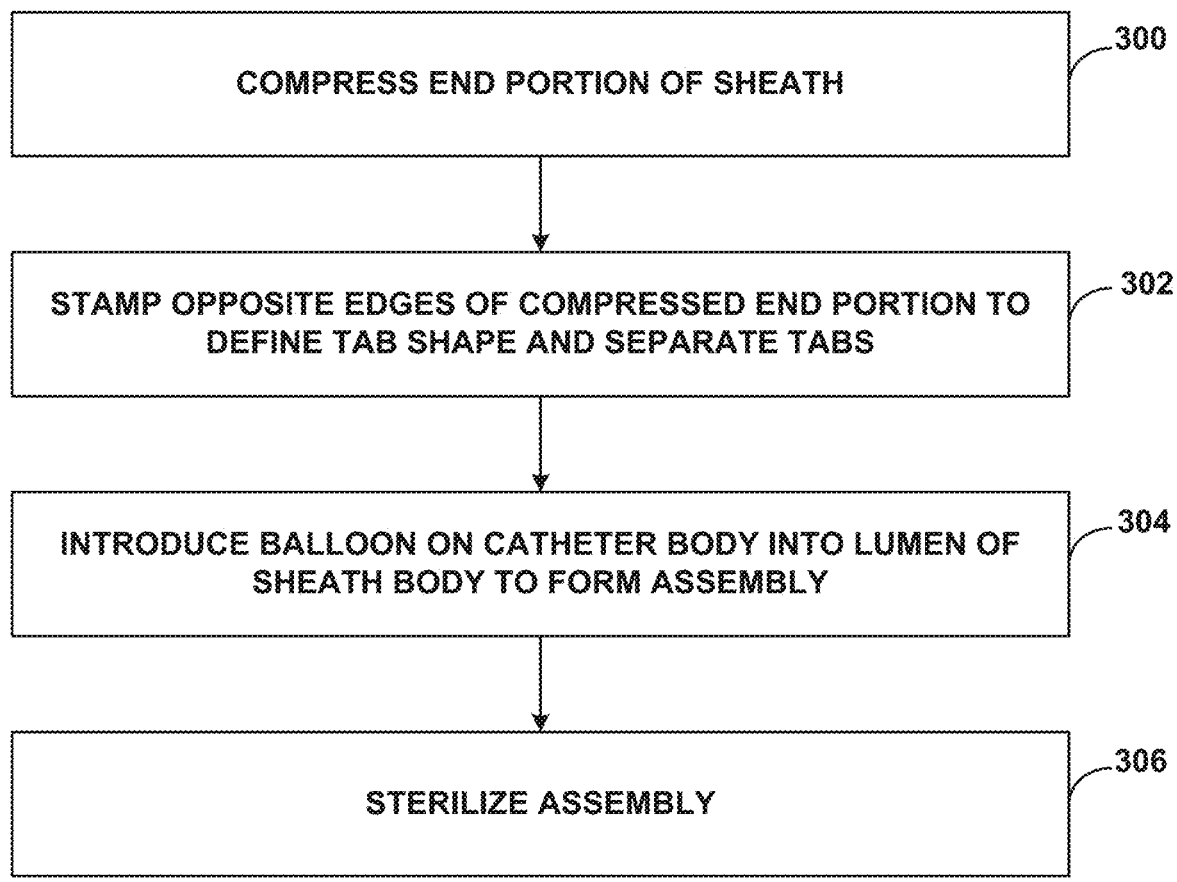
FIG. 15 is a flow diagram illustrating an example method of manufacturing a splittable sheath as described herein.

FIG. 15 is a flow diagram illustrating example technique that may be implemented to manufacture the example splittable sheaths described herein. The flow diagram of FIG. 15 is described in conjunction with FIGS. 16A-16C, which illustrate a series of side views showing the manufacture of example splittable sheaths using manufacturing equipment configured to receive a tubular "blank" sheath and output finished splittable sheaths having the tabs described herein. While FIG. 15 is described in context with the splittable sheath 12 of FIGS. 1-4D, the technique of FIG. 15 may be used to manufacture any of the other splittable sheaths described herein, such as the splittable sheaths of FIGS. 5A-12. Additionally, or alternatively, the technique of FIG. 15 may be used in conjunction with other techniques for manufacturing, cleaning, or sterilizing the splittable sheath 12 and other components of the medical device 10 of FIG. 1.

Figure 16A:
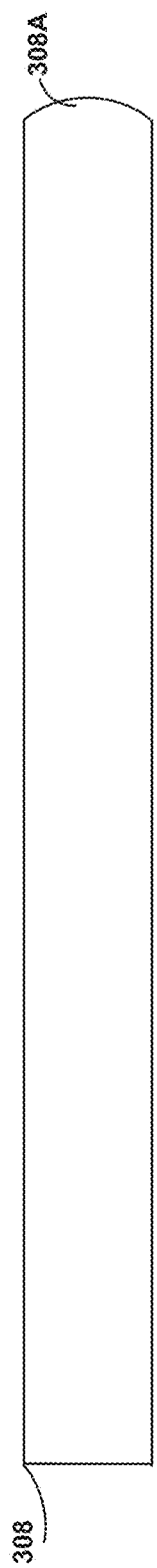
FIGS. 16A-16C are a series of perspective views showing an example splittable sheath being manufactured in accordance with the techniques described with respect to the example method of FIG. 15.
Figure 16B:
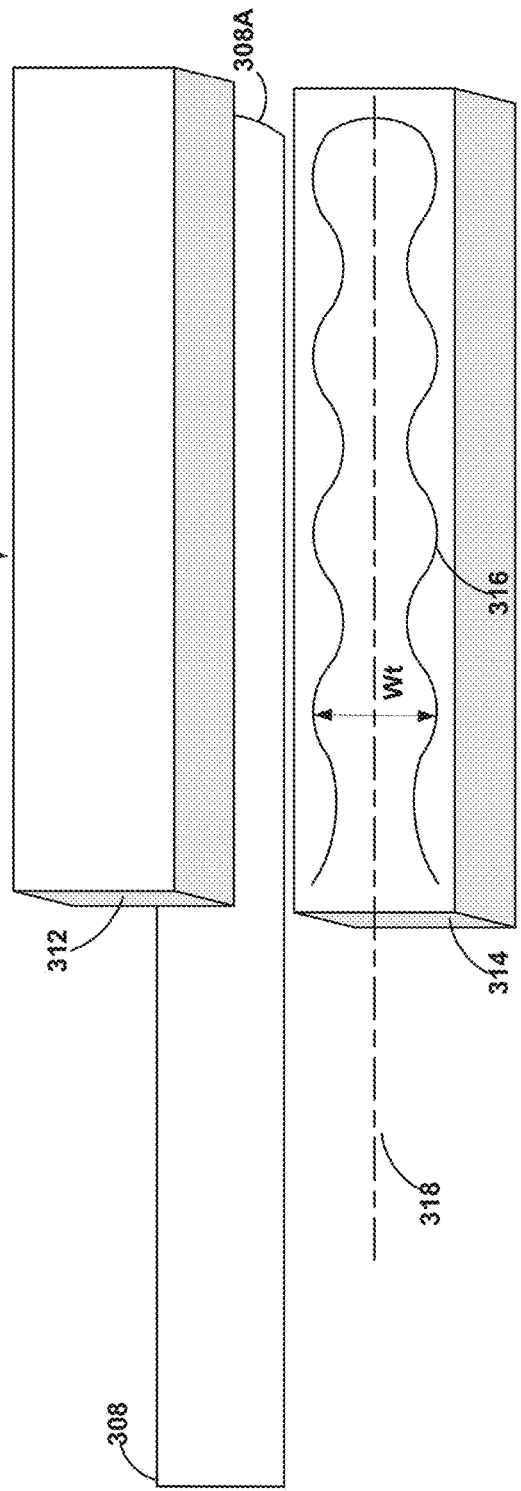

The technique of FIG. 15 includes introducing a tubular member 308, shown in FIG. 16A, into a manufacturing device 310, as shown in FIG. 16B. The tubular member 308 can include, for example, the desired inner lumen 18 of the sheath body 14, as well as sufficient length to form both the sheath body 14 and the tabs 16A, 16B from a common tubular member. In some examples, the tubular member 308 can be referred to as a tubular blank.

The manufacturing device 310 may include an upper block 312 and a lower block 314. In the example of FIG. 16B, the lower block 314 defines a tab form 316, which may be configured in the shape of the outer edges 19A, 19B of the tabs 16A, 16B. In some examples, upper block 312 may also define the tab form 316 in addition to or instead of lower block 314. The upper block 312 and lower block 314 may be two halves of a simple die set. In some examples, the tab form 316 may include a sharp cutting blade configured to cut through a material of the tubular member 308 to form the tabs 16A, 16B and define the tabs 16A, 16B and the sheath body 14 from the common tubular member 308. In other examples, the tab form 316 in the lower block 314 may be a recessed shaped like the tabs 16A, 16B, and the upper block 312 may include a protruding shape that fits into the recess in the lower block 314 to shear the material and form the tabs. In other examples, the tab form 316 may include an electrically-conductive strip through which an electric current may be passed to heat the tab form 316 to a temperature sufficient to soften the material of the splittable sheath 12 and aid in removing material from tubular member 308.

As illustrated in FIG. 16B, a greatest width $W_T$ (measured perpendicular to the central longitudinal axis 318 of the tab form 316 of the manufacturing device 310 may be less than or equal to the greatest dimension $W_S$ (described above with respect to FIGS. 4A-4D) of the lumen 18 of the sheath body 14. Thus, the technique of FIG. 15 may be configured to manufacture the splittable sheaths described herein by shearing off portions of material from a tubular member 308, instead of by adding material to a tubular member 308. Thus, the technique of FIG. 15 may be configured to manufacture the splittable sheaths described herein by shearing off portions of material from a tubular member 308, instead of by adding material to a tubular member 308.

In some examples, blocks 312, 314 are configured such that only a thickness equal to a wall thickness of the outer wall 29 (FIG. 4B) of the tubular member 308 is removed when tubular member 308 is compressed between the blocks 312, 314. This may help maximize the surface area of major surfaces 17A, 17B of the tabs 16A, 16B. When a thickness equal to a wall thickness of the outer wall 29 is removed from the tubular member 308, the tubular member 308 may be divided into two halves that are movable relative to each other, which define the tabs 16A, 16B. The wall thickness of the outer wall 29 represents the minimum amount of the tubular member 308 that needs to be removed in order to define the tabs 16A, 16B.

In some cases, it may be advantageous to manufacture the splittable sheaths described herein, by removing material to create desired shapes and configurations instead of adding material. For example, a process of removing material may eliminate a need for a bonding step that may be necessary in techniques that require adding material to an item, and may reduce the amount of material needed compared to techniques that include adding material to an item. Thus, savings in manufacturing time, labor time, and material usage may result from manufacturing techniques such as the technique of FIG. 15.

Figure 16C:
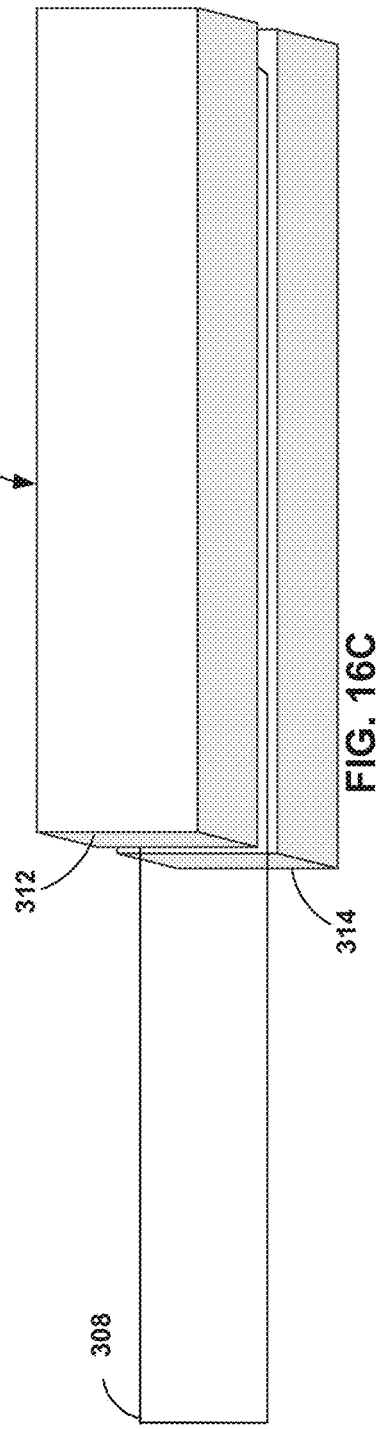

In FIG. 16C, a proximal portion of the tubular member 308 is positioned between the upper block 312 and the lower block 314 of the manufacturing device 310, with a proximal end 308A of the tubular member 308 between the blocks 312, 314. The upper block 312 and the lower block 314 then are brought together to compress a proximal portion of the tubular member (300), and stamp the compressed portion to define the shape of the outer edges 19A, 19B and separate the tabs 16A, 16B of the splittable sheath 12 (302). The finished splittable sheath 12 resulting from the method shown in FIG. 15 may look like splittable sheath 12 shown in FIGS. 4A-4D.

In some examples, the tab form 316 having the serpentine shape may be interchangeable with one or more other tab forms 316 configured to produce the outer-edge shapes described above with respect to the tabs of other example splittable sheaths of this disclosure. Thus, the manufacturing device 310 may be used to manufacture splittable sheaths having a variety of configurations and sizes, and may be adapted to produce other items whose manufacture may include the stamping or cutting of objects into desired shapes.

After the splittable sheath 12 has been stamped to form and separate the tabs 16A, 16B, the expandable balloon 50 positioned on the catheter 30 may be introduced into the lumen 18 of the sheath body 14 to form a sheathed balloon-and-catheter assembly (304). For example, a proximal end 34 of the catheter 30 may be fed through the lumen 18 of the sheath body 14 from the distal end 20 of the sheath body 14 to the proximal end 22 of the sheath body 14, followed by a portion of the catheter 30 on which the expandable balloon 50 is positioned. Once the expandable balloon 50 is received within the lumen 18 of the sheath body 14 and the proximal 34 portion of the catheter body 32 extends from the proximal end 22 of the sheath body, the hub 36 optionally may be attached to the proximal end 34 of the catheter body 32. Finally, the assembled medical device 10 may be sterilized (306) and packaged.

Various aspects of the disclosure have been described. These and other aspects are within the scope of the following claims.

What is claimed is:

1. A device comprising:
    a catheter comprising:
        a catheter body; and
        an expandable balloon positioned on the catheter body; and
    a splittable sheath comprising:
        a sheath body defining a lumen configured to receive the expandable balloon; and
        a tab extending from a proximal end or a distal end of the sheath body, wherein outward movement of the tab in a direction away from a central longitudinal axis of the sheath body causes splitting of the sheath body, and wherein the tab includes a major surface having an outer edge defining a serpentine shape,
        wherein the serpentine shape includes an outwardly-projecting portion extending away from the central longitudinal axis and away from the direction of the outward movement.

2. The device of claim 1, wherein a width of the tab is substantially the same as a width of the lumen of the sheath body, the width being measured in a direction perpendicular to the central longitudinal axis of the sheath body.

3. The device of claim 1, wherein the tab is integrally formed with the sheath body.

4. The device of claim 1, wherein the tab comprises a first tab including a first major surface having a first outer edge defining a first serpentine shape, the sheath further comprising a second tab extending from the proximal end or the distal end of the sheath body, wherein outward movement of the second tab relative to the first tab causes splitting of the sheath body, the second tab including a second major surface having a second outer edge defining a second serpentine shape.

5. The device of claim 4, wherein an outer wall of the sheath body defines at least one groove extending longitudinally along an outer surface of the sheath body, and wherein the sheath body is configured to split along the at least one groove when the first tab and the second tab are moved outward relative to the central longitudinal axis of the sheath body.

6. The device of claim 1, wherein an outer wall of the sheath body defines at least one groove extending longitudinally along an outer surface of the sheath body, and wherein the sheath body is configured to split along the at least one groove when the tab is moved outward relative to the central longitudinal axis of the sheath body.

7. The device of claim 6, wherein the at least one groove comprises a first groove and a second groove positioned on opposite sides of the central longitudinal axis of the sheath body.

8. The device of claim 6, wherein the at least one groove is aligned with the outer edge of the tab along an axis parallel to the central longitudinal axis of the sheath body.

9. The device of claim 6, wherein each groove of the at least one groove extends from the outer surface of the outer wall of the sheath body through about 50% to about 90% of a thickness of the outer wall of the sheath body.

10. The device of claim 6, wherein each groove of the at least one groove extends along about 2% to about 20% of a perimeter of a cross-section of the sheath body taken orthogonal to the central longitudinal axis of the sheath body.

11. The device of claim 1, wherein an outer wall of the sheath body comprises:
    an inner layer comprising a first material, the inner layer defining the lumen; and
    an outer layer comprising a second material that is different from the first material.

12. The device of claim 11, wherein a coefficient of friction of the first material is lower than a coefficient of friction of the second material.

13. The device of claim 11, wherein the second material has at least one of a compressive strength, a yield strength, or a tensile strength that is greater than at least one of a corresponding compressive strength, a yield strength, or a tensile strength of the first material.

14. The device of claim 11, wherein the first material comprises at least one of polytetrafluoroethylene (PTFE), high-density polyethylene (HDPE) or low-density polyethylene (LDPE).

15. The device of claim 11, further comprising a pharmacologically-active agent on an outer surface of the balloon or embedded in the balloon, wherein the first material is substantially chemically non-reactive with the pharmacologically-active agent.

16. The device of claim 11, wherein the second material comprises at least one of a polyamide or a polyamide block copolymer.

17. The device of claim 11, wherein the inner layer is about 10% to about 30% of a thickness of the outer wall of the sheath body.

18. The device of claim 11, wherein the outer layer is about 60% to about 90% of a thickness of the outer wall of the sheath body.

19. The device of claim 11, wherein the outer wall of the sheath body further includes an intermediate layer positioned between the inner layer and the outer layer, the intermediate layer comprising a material configured to bond the inner layer to the outer layer.

20. The device of claim 19, wherein the intermediate layer is about 5% to about 15% of a thickness of the outer wall of the sheath body.

21. A device comprising:
a catheter comprising:
a catheter body; and
an expandable balloon positioned on the catheter body; and
a splittable sheath comprising:
a sheath body defining a lumen configured to receive the expandable balloon, wherein an outer wall of the sheath body defines a groove extending longitudinally along an outer surface of the sheath body, the outer wall of the sheath body comprising:
an inner layer comprising a first material, the inner layer defining the lumen; and
an outer layer comprising a second material, wherein a coefficient of friction of the first material is lower than a coefficient of friction of the second material; and
a tab extending from a proximal end or a distal end of the sheath body, wherein outward movement of the tab in a direction away from a central longitudinal axis of the sheath body causes splitting of the sheath body along the groove, and wherein the tab includes a major surface having an outer edge defining a serpentine shape,
wherein the serpentine shape includes an outwardly-projecting portion extending in a direction away from the central longitudinal axis and away from the direction of the outward movement.

22. The device of claim 21, wherein the tab comprises a first tab including a first major surface having a first outer edge defining a first serpentine shape, the sheath further comprising a second tab extending from the proximal end or the distal end of the sheath body, wherein outward movement of the second tab relative to the first tab causes splitting of the sheath body, the second tab including a second major surface having a second outer edge defining a second serpentine shape.

23. The device of claim 21, wherein the second material has at least one of a compressive strength, a yield strength, or a tensile strength that is greater than at least one of a corresponding compressive strength, a yield strength, or a tensile strength of the first material.

24. The device of claim 21, wherein the groove extends from the outer surface of the outer wall of the sheath body through about 50% to about 90% of a thickness of the outer wall of the sheath body.

25. The device of claim 21, wherein each groove of the at least one groove extends along about 2% to about 20% of a perimeter of a cross-section of the sheath body taken orthogonal to the central longitudinal axis of the sheath body.

26. The device of claim 21, further comprising a pharmacologically-active agent on the outer surface of the balloon or embedded in the balloon, wherein the first material is substantially chemically non-reactive with the pharmacologically-active agent.

27. A device comprising:
a catheter comprising:
a catheter body; and
an expandable balloon positioned on the catheter body; and
a splittable sheath comprising:
a sheath body defining a lumen configured to receive the expandable balloon, wherein an outer wall of the sheath body defines a groove extending longitudinally along an outer surface of the sheath body, the outer wall of the sheath body comprising:
an inner layer comprising a first material, the inner layer defining the lumen;
an outer layer comprising a second material, wherein a coefficient of friction of the first material is lower than a coefficient of friction of the second material; and
an intermediate layer positioned between the inner layer and the outer layer, the intermediate layer comprising a material configured to bond the inner layer to the outer layer; and
a first tab extending from a proximal end or a distal end of the sheath body, the first tab including a first major surface having a first outer edge defining a first serpentine shape; and
a second tab extending from the proximal end or the distal end of the sheath body, wherein outward movement of the second tab away from a central longitudinal axis of the sheath body and relative to the first tab causes splitting of the sheath body along the groove, the second tab including a second major surface having a second outer edge defining a second serpentine shape,
wherein the second serpentine shape includes an outwardly-projecting portion extending in a direction away from the central longitudinal axis and away from the direction of the outward movement of the second tab.

28. The device of claim 27, wherein the second material has at least one of a compressive strength, a yield strength, or a tensile strength that is greater than at least one of a corresponding compressive strength, a yield strength, or a tensile strength of the first material.

* * * * *